(12) United States Patent
Kim et al.

(10) Patent No.: US 8,101,725 B2
(45) Date of Patent: Jan. 24, 2012

(54) MONOCLONAL ANTIBODIES TO BASIC FIBROBLAST GROWTH FACTOR

(75) Inventors: Kyung Jin Kim, Cupertino, CA (US); Lihong Wang, Palo Alto, CA (US); Hangil Park, San Francisco, CA (US); Maximiliano Vasquez, Palo Alto, CA (US)

(73) Assignee: Galaxy Biotech, LLC, Cupertino, CA (US)

(*) Notice: Subject to any disclaimer, the term of this patent is extended or adjusted under 35 U.S.C. 154(b) by 0 days.

(21) Appl. No.: 12/474,198

(22) Filed: May 28, 2009

(65) Prior Publication Data

US 2009/0304707 A1 Dec. 10, 2009

Related U.S. Application Data

(60) Provisional application No. 61/057,183, filed on May 29, 2008, provisional application No. 61/170,561, filed on Apr. 17, 2009.

(51) Int. Cl.
*C07K 16/22* (2006.01)
*A61K 39/395* (2006.01)

(52) U.S. Cl. ............. 530/388.1; 530/388.24; 424/141.1; 424/142.1; 424/145.1

(58) Field of Classification Search ........................ None
See application file for complete search history.

(56) References Cited

U.S. PATENT DOCUMENTS

| | | | |
|---|---|---|---|
| 7,288,406 B2 | 10/2007 | Bogin et al. | |
| 7,560,244 B2 | 7/2009 | Krolewski et al. | |
| 2003/0202975 A1 | 10/2003 | Tedder | |
| 2004/0063910 A1 | 4/2004 | Kavanaugh et al. | |
| 2007/0036797 A1 | 2/2007 | Kim et al. | |

FOREIGN PATENT DOCUMENTS

| | | |
|---|---|---|
| WO | WO91/06668 A1 | 5/1991 |
| WO | WO2009/148928 A1 | 12/2009 |

OTHER PUBLICATIONS

Immunobiology, The Immune System in Health and Disease, Third Edition, Janeway, and Travers, Ed., 1997.*
MacCallum et al. (J. Mol. Biol. 262:732-745 (1996)).*
de Pascalis et al. (Journal of Immunology 169, 3076-3084 (2002)).*
Casset et al. (BBRC 307, 198-205, (2003)).*
Vajdos et al. (J. Mol. Biol. 320, 415-428 (2002)).*
Holm et al (Mol. Immunol. 44: 1075-1084 (2007)).*
Chen et al. (J. Mol. Bio. 293, 865-881 (1999)).*
Wu et al. (J. Mol. Biol. 294, 151-162 (1999)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Aonuma et al., "Different Antitumor Activities of Anti-bFGF Neutralizing Antibodies: Heparin-Binding Domain Provides and Inefficient Epitope for Neutralization in Vivo," *Anticancer Res.* 19:4039-4044 (1999).

Auguste et al., "Inhibition of Fibroblast Growth Factor/Fibroblast Growth Factor Receptor Activity in Glioma Cells Impedes Tumor Growth by Both Angiogenesis-dependent and -independent Mechanisms", *Cancer Res.* 61: 1717-1726 (2001).
Baird, et al., "Immunoreactive Fibroblast Growth Factor (FGF) in a Transplantable Chondrosarcoma: Inhibition of Tumor Growth by Antibodies to FGF," *J. Cell. Biochem.* 30:79-85 (1986).
Coppola et al., "Effect of Intraperitoneally, Intravenously and Intralesionally Administered Monoclonal Anti-β-FGF Antibodies on Rat Chondrosarcoma Tumour Vascularization and Growth," *Anticancer Res.* 17:2033-2040 (1997).
Delrieu, "The high molecular weight isofroms of basic fibroblast growth factor (FGF-2): an insight into an intracrine mechanism," *FEBS Letters* 268:6-10 (2000).
Dow et al., "Fibroblast Growth Factor 2: Its Structure and Property, Paracrine Function, Tumor Angiogenesis, and Prostate-Related Mitogenic and Oncogenic Functions," *Urology* 55:800-806 (2000).
EMBL Accession No. S37484. Datasheet. Jan. 11, 2000, online at http://www.ncbi.nlm.nih.gov/protein/480896.
Gross et al., "Effects of Modulation of Basic Fibroblast Growth Factor on Tumor Growth In Vivo," *J. Nat'l Cancer Institute* 85(2):121-131 (1993).
Hori et al., "Suppression of Solid Tumor Growth by Immunoneutralizing Monoclonal Antibody against Human Basic Fibroblast Growth Factor," *Cancer Res.* 51:6180-6184 (1991).
Kuhn et al., "Influence of basic fibroblast growth factor on the proliferation of non-small cell lung cancer cell lines," *Lung Cancer* 44:167-176 (2004).
Kurokawa, et al., "Neutralizing Antibodies Inhibit the Binding of Basic Fibroblast Growth Factor to its Receptor but Not to Heparin," *J. Biol. Chem.* 263(13):7686-7691 (1989).
Lu et al., "Inhibitory Effect of Antibody against Basic Fibroblast Growth Factor on Androgenor Glucocorticoid-induced Growth of Shionogi Carcinoma 115 Cells in Serum-free Culture", *Cancer Res* 49: 4963-4967 (1989).
Matsuzaki et al., "Monoclonal antibodies against heparin-binding growth factor II/basic fibroblast growth factor that block its biological activity: Invalidity of the antibodies for tumor angiogenesis," *PNAS* 86:9911-9915 (1989).
Mohammadi et al., "Structural basis for fibroblast growth factor receptor activation," *Cytokine & Growth Factor Reviews* 16:107-137 (2005).
Morrison et al., "Fibroblast Growth Factor Receptor Gene Expression and Immunoreactivity Are Elevated in Human Glioblastoma Multiforme," *Cancer Res.* 54:2794-2799 (1994).
Morrison et al., "Basic Fibroblast Growth Factor Expression is Required for Clonogenic Growth of Human Glioma Cells," *J. Neurosci. Res.* 34:502-509 (1993).
Presta et al., "Fibroblast growth factor/fibroblast growth factor receptor system in angiogenesis," *Cytokine & Growth Factor Reviews* 16:159-178 (2005).

(Continued)

*Primary Examiner* — Christine J Saoud
(74) *Attorney, Agent, or Firm* — Alston and Bird LLP

(57) ABSTRACT

The present invention is directed toward a neutralizing monoclonal antibody to basic fibroblast growth factor, a pharmaceutical composition comprising same, and methods of treatment comprising administering such a pharmaceutical composition to a patient.

5 Claims, 13 Drawing Sheets

OTHER PUBLICATIONS

Reilly et al., "Monoclonal Antibodies Directed Against Basic Fibroblast Growth Factor which Inhibit its Biological Activity In Vitro and In Vivo," *Biochem. Biophys. Res. Comm.* 164(2):736-743 (1989).

Song et al., "Fibroblast growth factors: An epigenetic resistance to anticancer drugs," *PNAS* 97(15):8658-8663 (2000).

Okada-Ban et al., "Fibroblast growth factor-2," *Int'l J. Biochem. Cell Biol.* 32:263-267 (2000).

Ornitz, et al., "Receptor Specificity of the Fibroblast Growth Factor Family," *J. Biol. Chem.* 271(25):15292-15297 (1996).

Ornitz, et al., "Fibroblast growth factors," *Genome Biol.* 2(3):reviews 3005.1-3005.12 (2001).

Takahashi et al., "Gene expression of fibroblast growth factors in human gliomas and meningiomas: Demonstration of cellular source of basic fibroblast growth factor mRNA and peptide in tumor tissues," *PNAS* 87:5710-5714 (1990).

Takahashi et al., "Inhibition of cell growth and tumorgenesis of human glioblastoma cells by a neutralizing antibody against human basic fibroblast growth factor" *FEBS Letters* 288(1-2): 65-71 (1991).

Wang et al., "Antisense targeting of basic fibroblast growth factor and fibroblast growth factor receptor-1 in human melanomas blocks intratumoral angiogenesis and tumor growth," *Nature Med.* 3(8):887-893 (1997).

PCT/US09/45519, International Search Report mailed Oct. 9, 2009.

PCT/US09/45519, Written Opinion of the International Searching Authority mailed Oct. 9, 2009.

Kin et al., "Basic Fibroblast Growth Factor Regulates Proliferation and Mobility of Human Hepatoma Cells by an Autocrine Mechanism," *Journal of Hepatology*, 27:677-687 (1997).

Ogasawara et al., Expressions of Basic Filbroblast Growth Factor and Its Receptors and Their Relationships to Proliferation of Human Hepatocellular Carcinoma Cell Lines, *Heptaology*, 24(1): 198-205 (1996).

Poon et al., Correlation of Serum Basic Fibroblast Growth Factor Levels With Clinicopathologic Features and Postoperative Recurrence Hepatocellular Carcinoma, *The American Journal of Surgery*, 182:298-304 (2001).

Rege et al., "Development of Novek Monoclonal Antibodies for the Analysis of Functional Sites in FGF-2," *Growth Factors*, vol. 16:161-169 (1999).

\* cited by examiner

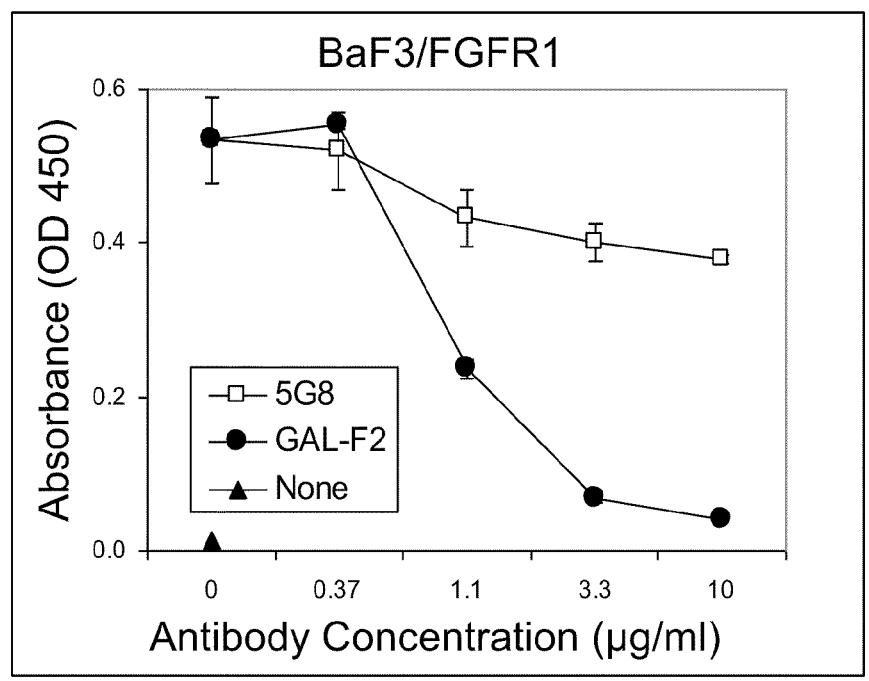
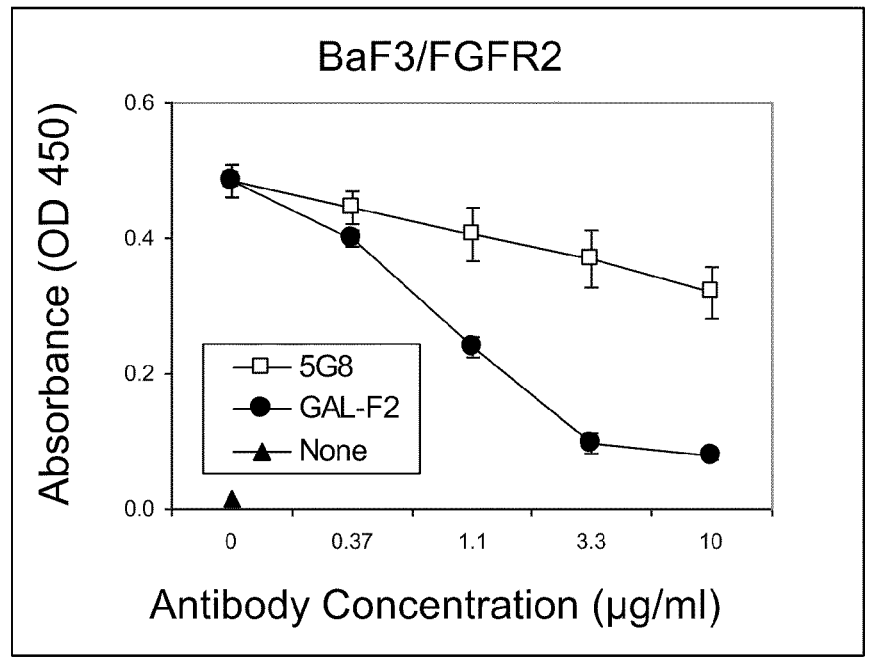
FIGURE 4

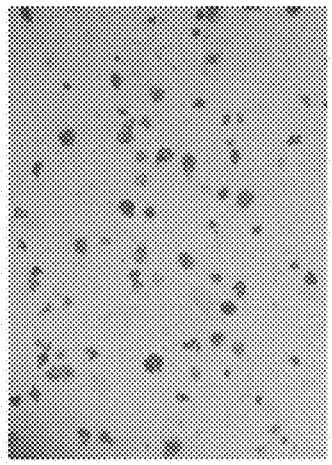 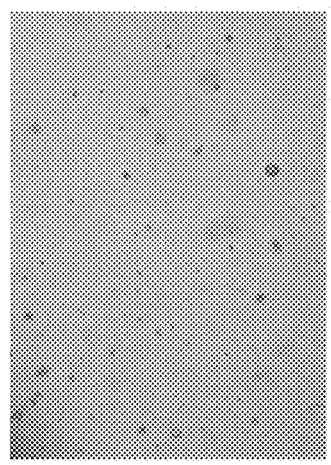 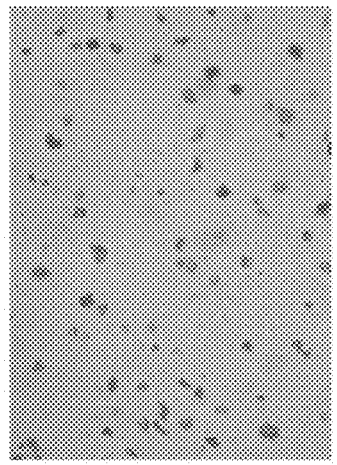
mIgG　　　　　　　　GAL-F2　　　　　　　　bFM-1
FIGURE 6

A

```
                        1          2          3          4
                   1234567890 1234567890 1234567890 1234567890
GAL-F2             SIVMTQTPKF LLVSAGDRVT MTCKASQSVS SDVGWYQQKP
HuGAL-F2           DIQMTQSPSS LSASVGDRVT ITCKASQSVS SDVGWYQQKP
ABA70776           DIQMTQSPSS LSASVGDRVT ITCrasqsis sylnWYQQKP 5          6          7          8
                   1234567890 1234567890 1234567890 1234567890
GAL-F2             GQSPKLLIYS GSNRYSGVPD RFTGSGYGTD FTFTISTVQA
HuGAL-F2           GKAPKLLIYS GSNRYSGVPS RFSGSGSGTD FTLTISSLQP
ABA70776           GKAPKLLIYa asslqsGVPS RFSGSGSGTD FTLTISSLQP 9         10
                   1234567890 1234567890 1234567
GAL-F2             EDLAVYFCQQ DYYSPWTFGG GTKLEIK
HuGAL-F2           EDFATYYCQQ DYYSPWTFGQ GTKVEIK
ABA70776           EDFATYYCqq systpwtFGQ GTKVEIK
```

B

```
                        1          2          3          4
                   1234567890 1234567890 1234567890 1234567890
GAL-F2             EVHLQQSGPE LVKPGASVKM SCKASGYTFT NYVINWVKQK
HuGAL-F2           EVQLVQSGAE VKKPGSSVKV SCKASGYTFT NYVINWVRQA
AAL04519           QVQLVQSGAE VKKPGSSVKV SCKASGGTFS syaisWVRQA 5      a       6          7          8
                   1234567890 12234567890 1234567890 1234567890
GAL-F2             PGQGLEWIGY NDPYNDVSKYN EKFKGKATLT SDKSSSTAYM
HuGAL-F2           PGQGLEWIGY NDPYNDVSKYN EKFKGRATIT SDKSTSTAYM
AAL04519           PGQGLEWMGg iipifgtanya qkfqgRVTIT ADKSTSTAYM abc        9         10ab cd       11
                   1222234567890 123456789000 00 1234567890123
GAL-F2             ELSSLTSEDSAVY YCAKEGGGKYVY AM DSWGQGTSVTVSS
HuGAL-F2           ELSSLRSEDTAVY YCAKEGGGKYVY AM DSWGQGTTVTVSS
AAL04519           ELSSLRSEDTAVY YCARvgqlgyyyygm dvWGQGTTVTVSS
```

MONOCLONAL ANTIBODIES TO BASIC FIBROBLAST GROWTH FACTOR

CROSS-REFERENCES TO RELATED APPLICATIONS

This applications claims the benefit under 35 U.S.C. §119 (e) of U.S. Patent Application No. 61/057,183 filed May 29, 2008 and U.S. Patent Application No. 61/170,561 filed Apr. 17, 2009, which are herewith incorporated in their entirety for all purposes.

STATEMENT AS TO RIGHTS TO INVENTIONS MADE UNDER FEDERALLY SPONSORED RESEARCH OR DEVELOPMENT

The work described in this application was funded in part by Grant 5R44 CA101283-03 from the National Institutes of Health. The US Government has certain rights in this invention.

REFERENCES TO A "SEQUENCE LISTING," A TABLE, OR A COMPUTER PROGRAM LISTING SUBMITTED IN COMPUTER READABLE FORMAT

The Sequence Listing written in file 397225_SEQLIST-.TXT is 3,136,198 bytes, and was created on Oct. 20, 2011. The information contained in this file is hereby incorporated by reference.

FIELD OF THE INVENTION

The present invention relates generally to the combination of monoclonal antibody (mAb) and recombinant DNA technologies for developing novel biologics, and more particularly, for example, to the production of monoclonal antibodies that bind to and neutralize basic Fibroblast Growth Factor.

BACKGROUND OF THE INVENTION

The prototypic Fibroblast Growth Factors (FGFs), acidic FGF (also called FGF1) and basic FGF (also called FGF2) were first isolated in the 1970s (FGF2 by Gospodarowicz et al., J. Biol. Chem. 250:2515, 1975). There are currently 22 known FGF family members, which can be grouped into 7 subfamilies based upon their similarity in activities and sequences (Ornitz et al., Genome Biol. 2: 3005.1, 2001). However, the FGF family members bind to only four tyrosine kinase receptors (FGFR14) and their isoforms, which are expressed in a tissue-specific manner. The FGF 1 subgroup consists of FGF 1 and FGF2, which bind all four FGFRs, with FGF2 binding especially strongly to FGFR1c (Ornitz et al., J. Biol. Chem. 271:15292, 1996).

Human FGF2 is an 18 kDa non-glycosylated polypeptide consisting of 146 amino acids in the mature form derived from a 155 aa precursor (Ornitz et al., Genome Biol. 2:3005.1, 2001; Okada-Ban et al., Int. J. Biochem. Cell. Biol. 32:263, 2000). This 18 kDa form of FGF2 does not encode a signal sequence, but can be secreted by an unconventional energy-dependent pathway independent of the ER-Golgi complex (Mignatti et al., J. Cell Physiol. 151:81, 1992; Florkiewicz et al., J. Cell Physiol. 162:388, 1995). The single copy of the FGF2 gene also encodes four High Molecular Weight (HMW) forms of the protein, in addition to the 18 kDa form, by utilizing four alternate CUG initiation sites that provide N-terminal extensions of various sizes, resulting in proteins of 22 kDa (196 aa), 22.5 kDa (201 aa), 24 kDa (210 aa) and 34 kDa (288 aa) (Florkiewicz et al., Proc. Natl. Acad. Sci. USA 86:3978, 1989; Prats et al., Proc. Natl. Acad. Sci. USA 86:1836, 1989). The HMW forms are not secreted but are transported to the cell nucleus where they can regulate cell growth or behavior in an intracrine fashion (Delrieu, FEBS Lett. 468:6, 2000).

In addition to binding FGFR1-4 with high affinity, FGF2 binds to heparin sulfate proteoglycans (HSPG) with lower affinity. Although FGF2 is secreted as a monomer, cell surface HSPG dimerizes FGF2 in a non-covalent side-to-side configuration that is subsequently capable of dimerizing and activating FGF receptors (Mohammadi et al., Cytokine Growth Factor Rev 16:107, 2005). The binding of FGF and HSPG to the extracellular domain of FGFR induces receptor dimerization, activation and autophosphorylation.

The FGFs, and in particular FGF2, have a broad spectrum of activities on various cell types (Ornitz et al., Genome Biol. 2:3005.1, 2001). FGF2 stimulates proliferation of (i.e., is mitogenic for) certain cells including fibroblasts and endothelial cells and is a survival factor (anti-apoptotic) for certain cells such as neural cells (Okada-Ban, op. cit.). It also stimulates differentiation (morphogenesis) and migration (motility) of endothelial cells (Dow et al., Urology 55:800, 2000). FGF2 is involved in development, especially of the nervous system. Importantly, FGF2 is a powerful angiogenic factor (Presta et al., Cytokine and Growth Factor Rev. 16:159, 2005).

FGF2 and other FGFs are believed to play a role in cancer, both by stimulating angiogenesis and tumor cells directly (Presta et al., op cit.) During tumor progression, cancer cells may respond to the extracellular FGF2 secreted from the stromal cells (paracrine), and then the tumor cells themselves may secrete FGF2 and respond to it in an autocrine manner. FGF2 or its receptor FGFR1 has been shown to be expressed or overexpressed in most gliomas (Takahashi et al., Proc. Natl. Acad. Sci. USA 87:5710, 1990; Morrison et al. Cancer Res. 54:2794, 1994). FGF2 is involved in progression of prostate tumors (Dow et al., Urology 55:800, 2000) and is a key mediator of the proliferation of malignant melanomas (Wang et al., Nature Med. 3:887, 1997). Over-expression and/or involvement of FGF2 or FGFR1 in tumor progression has also been reported for salivary gland tumors (Myoken et al., J. Path. 178:429, 1996), esophageal cancer (Barclay et al., Clin. Cancer Res. 11:7683, 2005), and thyroid carcinomas (Boelaert et al., J. Clin. Endocrin. Metabol. 88:2341, 2003).

Polyclonal antibodies (antiserum) to FGF2 have been reported to inhibit tumor growth of a transplantable chondrosarcoma in mice (Baird et al., J. Cell Biochem. 30:79, 1986), neutralize various activities of FGF2 in vitro (Kurokawa et al., J. Biol. Chem. 264:7686, 1989), and to inhibit growth of U87 glioma cell intracranial xenografts when applied locally (Stan et al., J. Neurosurg. 82:1044, 1995). Among monoclonal antibodies, the DG2 mAb has been reported to neutralize activities of FGF2 in vitro and in vivo (Reilly et al., Biochem. Biophys. Res. Com. 164:736, 1989; WO 91/06668), modestly inhibit growth of rat C6 glioma xenografts in nude mice (Gross et al., J. Nat. Cancer Inst. 85:121, 1993), and modestly inhibit growth of rat chondrosarcomas when delivered intralesionally but not i.p. or i.v. (Coppola et al., Anticancer Res. 17:2033, 1997). Similarly, anti-FGF2 mAb DE6 has been reported to inhibit growth of glioma cells in vitro (Morrison et al., J. Neuroscience Res. 34:502, 1993). On the other hand, the anti-FGF2 mAbs bFM-1 and bFM-2 was reported to inhibit growth of endothelial cells in vitro but not to block tumor angiogenesis in vivo (Matsuzaki et al., Proc. Natl. Acad. Sci. USA 86:9911, 1989).

The neutralizing anti-FGF2 mAb 1E6 has been reported to inhibit growth of RPMI4788 colon tumor xenografts (Aonuma et al., 19:4039, 1999). The anti-FGF2 mAb 254F1 has been reported to inhibit proliferation of human umbilical vein endothelial cells (HUVEC), while mAb FB-8 has been reported to inhibit proliferation of non-small cell lung cancer cell lines in vitro (Kuhn et al., Lung Cancer 44:167, 2004). The anti-FGF2 mAb 3H3 was reported to suppress growth of U87MG and T98G glioma and HeLa cell xenografts (Takahashi et al., FEBS Let. 288:65, 1991) and growth of the K1000 FGF2-transfected 3T3 cell line in mice (Hori et al., Cancer Res. 51:6180, 1991).

The GAL-F2 anti-FGF2 mAb described herein was discussed at the AACR 2009 Annual Meeting in Poster #1236, which is incorporated herein in its entirety for all purposes.

BRIEF SUMMARY OF THE INVENTION

In one embodiment, the invention provides a neutralizing mAb to human basic fibroblast growth factor (FGF2). The mAb inhibits at least one, and preferably several or all biological activities of FGF2, including binding to one or more of the four FGF receptors FGFR1-4; inducing proliferation of fibroblasts, endothelial cells, Mv 1 Lu mink lung epithelial cells, and/or various human tumor cells; and inducing angiogenesis. The anti-FGF2 mAb can inhibit such an activity when used as a single agent. A preferred anti-FGF2 mAb inhibits growth of a human tumor xenograft in a mouse. Preferably, the mAb of the invention is genetically engineered, e.g., chimeric, humanized or human. Exemplary antibodies are GAL-F2 and its chimeric and humanized forms, and mAbs which have the same epitope or compete for binding with GAL-F2. Cell lines producing such antibodies are also provided. In another embodiment, a pharmaceutical composition comprising a neutralizing anti-FGF2 antibody, e.g., chimeric or humanized GAL-F2, is provided. In a third embodiment, the pharmaceutical composition is administered to a patient to treat cancer or other disease.

BRIEF DESCRIPTION OF THE DRAWINGS

FIG. 4. Inhibition of FGF2-induced proliferation of BaF3 cells stably transfected with FGFR1 or FGFR2, by GAL-F2 or control mAb 5G8. None means that no FGF2 (or mAb) was applied to the cells.

FIG. 6. Photomicrographs of SMCC-7721 cells cloned in soft agar in the presence of control mouse mAb (mIgG), GAL-F2 or bFM-1 anti-FGF2 mAb.

FIGS. 11A and 11B. Amino acid sequences of the HuGAL-F2 light chain (A) (SEQ ID NO:2) and heavy chain (B) mature variable regions (SEQ ID NO:5) are shown aligned with mouse GAL-F2 (SEQ ID NOS:1 and 4) and human acceptor V regions (SEQ ID NOS:3 and 6). The CDRs are underlined in the GAL-F2 sequences, and the amino acids substituted with mouse L2G7 amino acids are double underlined in the HuGAL-F2 sequences. The 1-letter amino acid code and Kabat numbering system are used for both the light and heavy chain.

FIG. 13. Amino acid sequences of the entire mature HuGAL-F2 antibody light chain (A) (SEQ ID NO:7) and heavy chain (B) (SEQ ID NO:8). The first amino acid on each line is numbered; the numbering is sequential. In the light chain, the first amino acid of the Cκ region is underlined, and in the heavy chain, the first amino acids of the CH1, hinge, CH2 and CH3 regions are underlined.

DETAILED DESCRIPTION OF THE INVENTION

Figure 1:
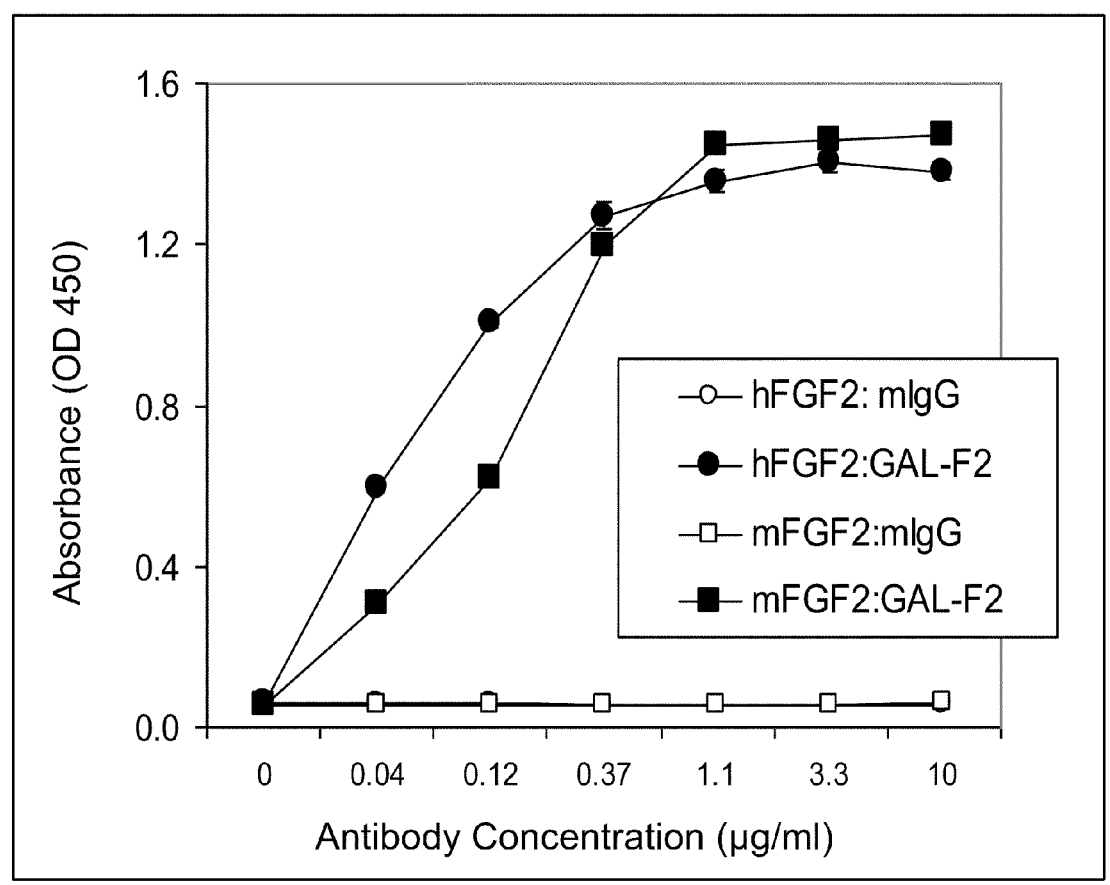
FIG. 1. Binding ELISA of GAL-F2 and control mouse mAb (mIgG) to human FGF2 (hFGF2) and mouse FGF29 (mFGF2).

The invention provides neutralizing anti-FGF2 monoclonal antibodies, pharmaceutical compositions comprising them, and methods of using them for the treatment of disease.

1. Antibodies

Antibodies are very large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarily determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework, which forms the environment for the CDRs. Chothia et al., J. Mol. Biol. 196:901, 1987, have defined the related concept of hypervariable regions or loops determined by structure.

A humanized antibody is a genetically engineered antibody in which the CDRs from a mouse antibody ("donor antibody", which can also be rat, hamster or other non-human species) are grafted onto a human antibody ("acceptor antibody"). The sequence of the acceptor antibody can be, for example, a mature human antibody sequence, a consensus sequence of human antibody sequences or a germline sequence. Thus, a humanized antibody is an antibody having CDRs from a donor antibody and variable region framework and constant regions from a human antibody. In addition, in order to retain high binding affinity, at least one of two additional structural elements can be employed. See, U.S. Pat. Nos. 5,530,101 and 5,585,089, incorporated herein by reference, which provide detailed instructions for construction of humanized antibodies. A humanized antibody typically has a humanized heavy chain and a humanized light chain In general neither the heavy chain variable region framework of a humanized heavy chain nor the light chain variable region framework of a humanized light chain includes more than ten or twelve substitutions resulting in residues not present in the acceptor human heavy or light chain variable region framework (including human consensus variable region frameworks and composite human variable region frameworks).

Although humanized antibodies often incorporate all six intact CDRs (as defined by Kabat) from a mouse antibody, they can also be made with less than the complete CDRs from a mouse antibody (e.g., Pascalis et al., J. Immunol. 169:3076, 2002). Numerous antibodies have been described in the scientific literature in which one or two CDRs can be dispensed with for binding. Padlan et al., FASEB Journal 9: 133-139 (1995); Vajdos et al., Journal of Molecular Biology, 320: 415-428 (2002); Iwahashi et al., Mol. Immunol. 36:1079-1091, (1999); Tamura et al, Journal of Immunology, 164: 1432-1441 (2000). Similarly, it may be necessary to incorporate only part of the CDRs, namely the subset of CDR residues required for binding, termed the SDRs, into the humanized antibody.

CDR residues not contacting antigen and not in the SDRs can be identified based on previous studies (for example residues H60-H65 in CDRH2 are often not required), from regions of Kabat CDRs lying outside Chothia hypervariable loops, by molecular modeling and/or empirically, or as described in Gonzales et al., Mol. Immunol. 41: 863, 2004. If a CDR or residue(s) thereof is omitted, it is usually substituted with an amino acid occupying the corresponding position in the human acceptor sequence supplying the variable region framework sequences. The number of such substitutions to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

In the first structural element referred to above for retaining high binding affinity in a humanized antibody, the framework of the heavy chain variable region of the humanized antibody is chosen to have maximal sequence identity (between 65% and 95%) with the framework of the heavy chain variable region of the donor antibody, by suitably selecting the acceptor antibody from among the many known human antibodies. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

As used herein, the term "human-like" antibody refers to a mAb in which a substantial portion of the amino acid sequence of one or both chains (e.g., about 50% or more) originates from human immunoglobulin genes. Hence, human-like antibodies encompass but are not limited to chimeric, humanized and human antibodies. As used herein, a mAb with "reduced immunogenicity" is one expected to have significantly less immunogenicity than a mouse antibody when administered to human patients. Such antibodies encompass chimeric, humanized and human mAbs as well as mAbs made by replacing specific amino acids in mouse antibodies that may contribute to B- or T-cell epitopes, for example exposed residues (Padlan, Mol. Immunol. 28:489, 1991). As used herein, a "genetically engineered" mAb is one for which the genes have been constructed or put in an unnatural environment (e.g., human genes in a mouse or on a bacteriophage) with the help of recombinant DNA techniques, and would therefore, e.g., not encompass a mouse mAb made with conventional hybridoma technology.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay (see, e.g., Junghans et al., Cancer Res. 50:1495, 1990). Alternatively, two antibodies have the same epitope if they bind the same region of the antigen or if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

2. Neutralizing Anti-FGF2 Antibodies

A monoclonal antibody (mAb) that binds FGF2 (i.e., an anti-FGF2 mAb) is said to neutralize FGF2, or be neutralizing, if the binding partially or completely inhibits one or more biological activities of FGF2 (i.e., when the mAb is used as a single agent). Among the biological properties of FGF2 that a neutralizing antibody may inhibit are the ability of FGF2 to bind to one or more of the four FGF receptors, to stimulate proliferation of (i.e., be mitogenic for) certain cells including fibroblasts, endothelial cells, Mv 1 Lu mink lung epithelial cells, and various human tumor cells; to stimulate differentiation and migration of cells such as endothelial cells, or to stimulate angiogenesis, for example as measured by stimulation of human vascular endothelial cell (HUVEC) proliferation or tube formation or by induction of blood vessels when applied to the chick embryo chorioallantoic membrane (CAM).

A neutralizing mAb of the invention at a concentration of, e.g., 0.01, 0.1, 0.5, 1, 2, 5, 10, 20 or 50 µg/ml inhibits a biological function of FGF2 by about at least 50% but preferably 75%, more preferably by 90% or 95% or even 99%, and most preferably approximately 100% (essentially completely) as assayed by methods described under Examples or known in the art. Typically, the extent of inhibition is measured when the amount of FGF2 used is just sufficient to fully stimulate the biological activity, or is 1, 2, or 5 ng/ml or 0.01, 0.02, 0.05, 0.1, 0.5, 1, 3 or 10 µg/ml. Preferably, the mAb is neutralizing, i.e., inhibits the biological activity, when used as a single agent, but optionally 2 mAbs can be used together to give inhibition. Most preferably, the mAb neutralizes not just one but two, three or several of the biological activities listed above; for purposes herein, an anti-FGF2 mAb that used as a single agent neutralizes all the biological activities of FGF2 is called "fully neutralizing", and such mAbs are most preferable. MAbs of the invention are preferably specific for FGF2, that is they do not bind, or only bind to a much lesser extent (e.g., at least 10-fold less), proteins that are related to FGF2 such as the other FGFs, e.g., FGF 1, and vascular endothelial growth factor (VEGF). Some mAbs of the invention bind both human FGF2 and mouse FGF2, or bind human FGF2 and one, two or more or all of mouse, rat, rabbit, chicken, dog and/or monkey (e.g., cynomolgus monkey) FGF2. Other mAbs are specific for human FGF2. MAbs of the invention typically have a binding affinity (Ka) for FGF2 of at least $10^7$ $M^{-1}$ but preferably $10^8$ $M^{-1}$ or higher, and most preferably $10^9$ $M^{-1}$ or higher or even $10^{10}$ $M^{-1}$ or higher.

MAbs of the invention include anti-FGF2 antibodies in their natural tetrameric form (2 light chains and 2 heavy chains) and may be of any of the known isotypes IgG, IgA, IgM, IgD and IgE and their subtypes, i.e., human IgG1, IgG2, IgG3, IgG4 and mouse IgG1, IgG2a, IgG2b, and IgG3. The mAbs of the invention are also meant to include fragments of antibodies such as Fv, Fab and F(ab')2; bifunctional hybrid antibodies (e.g., Lanzavecchia et al., Eur. J. Immunol. 17:105, 1987), single-chain antibodies (Huston et al., Proc. Natl. Acad. Sci. USA 85:5879, 1988; Bird et al., Science 242:423, 1988); single-arm antibodies (Nguyen et al., Cancer Gene Ther. 10:840, 2003); and antibodies with altered constant regions (e.g., U.S. Pat. No. 5,624,821). The mAbs may be of animal (e.g., mouse, rat, hamster or chicken) origin, or they may be genetically engineered. Rodent mAbs are made by standard methods well-known in the art, comprising multiple immunization with FGF2 in appropriate adjuvant i.p., i.v., or into the footpad, followed by extraction of spleen or lymph node cells and fusion with a suitable immortalized cell line, and then selection for hybridomas that produce antibody binding to FGF2, e.g., see under Examples. Chimeric and humanized mAbs, made by art-known methods mentioned supra, are preferred embodiments of the invention. Human antibodies made, e.g., by phage display or transgenic mice methods are also preferred (see e.g., Dower et al., McCafferty et al., Winter, Lonberg et al., Kucherlapati, supra).

The neutralizing anti-FGF2 mAb GAL-F2 described infra is an example of the invention. Once a single, archetypal anti-human-FGF2 mAb, for example GAL-F2, has been isolated that has the desired properties described herein of neutralizing FGF2, it is straightforward to generate other mAbs with similar properties, by using art-known methods. For example, mice may be immunized with FGF2 as described above, hybridomas produced, and the resulting mAbs screened for the ability to compete with the archetypal mAb for binding to FGF2. Mice can also be immunized with a smaller fragment of FGF2 containing the epitope to which GAL-F2 binds. The epitope can be localized by, e.g., screening for binding to a series of overlapping peptides spanning FGF2. Alternatively, the method of Jespers et al., Biotechnology 12:899, 1994, which is incorporated herein by reference, may be used to guide the selection of mAbs having the same epitope and therefore similar properties to the archetypal mAb, e.g., GAL-F2. Using phage display, first the heavy chain of the archetypal antibody is paired with a repertoire of (preferably human) light chains to select an FGF2-binding mAb, and then the new light chain is paired with a repertoire of (preferably human) heavy chains to select a (preferably human) FGF2-binding mAb having the same epitope as the archetypal mAb. Alternatively variants of GAL-F2 can be obtained by mutagenesis of cDNA encoding the heavy and light chains of GAL-F2 obtained from the hybridoma.

Neutralizing mAbs with the same or overlapping epitope as GAL-F2, e.g., that compete for binding to FGF2 with GAL-F2, provide other examples. A chimeric or humanized form of GAL-F2 is an especially preferred embodiment. MAbs that are 90%, 95% or 99% identical to GAL-F2 in amino acid sequence of the heavy and/or light chain variable regions and maintain its functional properties, and/or which differ from it by a small number of functionally inconsequential amino acid substitutions (e.g., conservative substitutions), deletions, or insertions are also included in the invention. MAbs having at least one and preferably all six CDR(s) that are 90%, 95% or 99% or 100% identical to corresponding CDRs of GAL-F2 are also included. Here, as elsewhere in this application, percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Native mAbs of the invention may be produced from their hybridomas. Genetically engineered mAbs, e.g., chimeric or humanized mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies selected by appropriate antibiotic selection. See, e.g., U.S. Pat. No. 5,530,101. Larger amounts of antibody may be produced by growing the cells in commercially available bioreactors.

Once expressed, the mAbs or other antibodies of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and 98% or 99% or more homogeneity most preferred, for pharmaceutical uses.

3. Treatment Methods

The invention provides methods of treatment in which the mAb of the invention (e.g., anti-FGF2) is administered to patients having a disease (therapeutic treatment) or at risk of occurrence or recurrence of a disease (prophylactic treatment). The term "patient" includes human patients; veterinary patients, such as cats, dogs and horses; farm animals, such as cattle, sheep, and pigs; and laboratory animals used for testing purposes, such as mice and rats. The methods are particularly amenable to treatment of human patients. The mAb used in methods of treating human patients binds to the human FGF2 protein, the sequence of which is provided by, e.g., Ornitz et al., Genome Biol. 2: 3005.1, 2001 or Okada-Ban et al., Int. J. Biochem. Cell. Biol. 32:263, 2000, also Locus P09038 of Swiss-Prot database. A mAb to a human protein can also be used in other species in which the species homolog has antigenic crossreactivity with the human protein. In species lacking such crossreactivity, an antibody is used with appropriate specificity for the species homolog present in that species. However, in xenograft experiments in laboratory animals, a mAb with specificity for the human protein expressed by the xenograft is generally used.

In a preferred embodiment, the present invention provides a pharmaceutical formulation comprising the antibodies described herein. Pharmaceutical formulations of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art (Remington's Pharmaceutical Science 16th edition, Osol, A. Ed. 1980). The mAb is typically present at a concentration of 1-100 mg/ml, e.g., 10 mg/ml.

In another preferred embodiment, the invention provides a method of treating a patient with a disease using an anti-FGF2 mAb in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given is sufficient at least partially to alleviate the condition being treated ("therapeutically effective dose") and is optionally 0.1 to 5 mg/kg body weight, for example 1, 2, 3 or 4 mg/kg, but may be as high as 10 mg/kg or even 15, 20 or 30 mg/kg. A fixed unit dose may also be given, for example, 100, 200, 500, 1000 or 2000 mg, or the dose may be based on the patient's surface area, e.g., 1000 mg/m$^2$. Usually between 1 and 8 doses, (e.g., 1, 2, 3, 4, 5, 6, 7 or 8) are administered to treat cancer, but 10, 20 or more doses may be given. The mAb can be administered daily, biweekly, weekly, every other week, monthly or at some other interval, depending, e.g. on the half-life of the mAb, for 1 week, 2 weeks, 4 weeks, 8 weeks, 3-6 months or longer or until the disease progresses. Repeated courses of treatment are also possible, as is chronic administration.

A combination of a dose, frequency of administration and route of administration effective to at least partially alleviate a disease present in a patient being treated is referred to as therapeutically effective regime. A combination of a dose, frequency of administration and route of administration effective to inhibit or delay onset of a disease in a patient is referred to as a prophylactically effective regime.

Diseases especially susceptible to treatment with the anti-FGF2 mAbs of this invention include solid tumors believed to require angiogenesis, or to be associated with elevated levels of FGF2, or to be associated with expression of FGF2. Such tumors, for which treatment with the anti-FGF2 mAb is appropriate, include for example ovarian cancer, breast cancer, lung cancer (small cell or non-small cell), colon cancer, prostate cancer, cervical cancer, endometrial cancer, pancreatic cancer, gastric cancer, hepatocellular carcinoma or hepatoma (liver cancer), head-and-neck tumors, melanoma, sarcomas, carcinomas, and brain tumors (e.g., gliomas such as glioblastomas). Hematologic malignancies such as leukemias and lymphomas and multiple myeloma can also be susceptible to such treatment. Other diseases associated with angiogenesis for which treatment with the anti-FGF mAbs of the invention are suitable include age-related macular degeneration (AMD), diabetic retinopathy, neovascular glaucoma and other diseases of the eye; psoriasis and other diseases of the skin; and rheumatoid arthritis.

In a preferred embodiment, the anti-FGF2 mAb is administered in combination with (i.e., together with, that is, before, during or after) other therapy. For example, to treat cancer, the anti-FGF2 mAb may be administered together with any one or more of the known chemotherapeutic drugs, for example alkylating agents such as carmustine, chlorambucil, cisplatin, carboplatin, oxaliplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; the topoisomerase 1 inhibitor irinotecan; agents specifically approved for brain tumors including temozolomide and Gliadel® wafer containing carmustine; and inhibitors of tyrosine kinases such as Gleevec® (imatinib mesylate), Sutent® (sunitinib malate), Nexavar® (sorafenib), Tarceva® (erlotinib) and Iressa® (gefitinib); inhibitors of angiogenesis; and all approved and experimental anti-cancer agents listed in WO 2005/017107 A2 (which is herein incorporated by reference). The anti-FGF2 mAb may be used in combination with 1, 2, 3 or more of these other agents used in a standard chemotherapeutic regimen. Normally, the other agents are those already known to be effective for the particular type of cancer being treated. The anti-FGF2 mAb is especially useful in overcoming resistance to chemotherapeutic drugs and thereby increasing their effectiveness (see Song et al. Proc. Natl. Acad. Sci USA 97:8658, 2000).

Other agents with which the anti-FGF2 mAb can be administered to treat cancer include biologics such as monoclonal antibodies, including Herceptin™ against the HER2 antigen; Avastin® against VEGF; or antibodies to the Epidermal Growth Factor (EGF) receptor such as Erbitux® (cetuximab) and Vectibix® (panitumumab). Antibodies against Hepatocyte Growth Factor (HGF) are especially preferred for use with the anti-FGF2 mAb, including mAb L2G7 (Kim et al., Clin Cancer Res 12:1292, 2006 and U.S. Pat. No. 7,220,410) and particularly its chimeric and humanized forms such as HuL2G7 (WO 07115049 A2); the human anti-HGF mAbs described in WO 2005/017107 A2, particularly 2.12.1; and the HGF binding proteins described in WO 07143090 A2 or WO 07143098 A2; and other neutralizing anti-HGF mAbs that compete for binding with any of the aforementioned mAbs. A mAb that binds the cMet receptor of HGF is also preferred, for example the anti-cMet mAb OA-5D5 (Martens et al., Clin. Cancer Res. 12:6144, 2006) that has been genetically engineered to have only one "arm", i.e. binding domain. Moreover, the anti FGF2 mAb can be used together with any form of surgery and/or radiation therapy including external beam radiation, intensity modulated radiation therapy (IMRT) and any form of radiosurgery such as, e.g. Gamma Knife.

Treatment (e.g., standard chemotherapy) including the anti-FGF2 mAb antibody may alleviate a disease by increasing the median progression-free survival or overall survival time of patients with cancer by at least 30% or 40% but preferably 50%, 60% to 70% or even 100% or longer, compared to the same treatment (e.g., chemotherapy) but without the anti-FGF2 mAb. In addition or alternatively, treatment (e.g., standard chemotherapy) including the anti-FGF2 mAb may increase the complete response rate, partial response rate, or objective response rate (complete+partial) of patients with these tumors (e.g., ovarian, breast, lung, colon and glioblastomas especially when relapsed or refractory) by at least 30% or 40% but preferably 50%, 60% to 70% or even 100% compared to the same treatment (e.g., chemotherapy) but without the anti-FGF2 mAb.

Typically, in a clinical trial (e.g., a phase II, phase II/III or phase III trial), the aforementioned increases in median progression-free survival and/or response rate of the patients treated with chemotherapy plus the anti-FGF2 mAb, relative to the control group of patients receiving chemotherapy alone (or plus placebo), are statistically significant, for example at the $p=0.05$ or $0.01$ or even $0.001$ level. The complete and partial response rates are determined by objective criteria commonly used in clinical trials for cancer, e.g., as listed or accepted by the National Cancer Institute and/or Food and Drug Administration.

4. Other Methods

The anti-FGF2 mAbs of the invention also find use in diagnostic, prognostic and laboratory methods. They may be used to measure the level of FGF2 in a tumor or in the circulation of a patient with a tumor, to determine if the level is measurable or even elevated, and therefore to follow and guide treatment of the tumor, since tumors associated with measurable or elevated levels of FGF2 will be most susceptible to treatment with the anti-FGF2 mAb. For example, a tumor associated with high levels of FGF2 would be especially susceptible to treatment with an anti-FGF2 mAb. In particular embodiments, the mAbs can be used in an ELISA or radioimmunoassay to measure the level of FGF2, e.g., in a tumor biopsy specimen or in serum or in media supernatant of FGF2-secreting cells in cell culture. The use of two anti-FGF2 mAbs binding to different epitopes (i.e., not competing for binding) will be especially useful in developing a sensitive "sandwich" ELISA to detect FGF2. For various assays, the mAb may be labeled with fluorescent molecules, spin-labeled molecules, enzymes or radioisotopes, and may be provided in the form of kit with all the necessary reagents to perform the assay for FGF2. In other uses, the anti-FGF2 mAbs will be used to purify FGF2, e.g., by affinity chromatography.

EXAMPLES

Example 1

Reagents and Assays

Preparation of GST-FGF2, FGF2-Fc and FGF2-Flag. The cDNA sequence for human FGF2 (the precursor form with 155 amino acids; Sommer et al., 1987) was synthesized (GenScript, Inc), PCR amplified and cloned into a derivative of the pDisplay vector (Invitrogen). These plasmids were transformed into E. coli BL21(DE3) cells and FGF2 expression was induced using 1 mM IPTG. The level of FGF2 expression was determined using an FGF2 specific ELISA Kit (R&D Systems), and FGF2 was purified using heparin-Sepharose CL-6B beads (Amersham Biosciences) as described (Wiedlocha et al., Mol. Cell Biol. 16:270, 1996). Fusion proteins of FGF2 with respectively glutamine synthetase (GST-FGF2), Flag peptide (FGF2-Flag), and human IgG1 Fc domain (amino acids 216 to 446; FGF2-Fc), which were used in the FGF2/FGFR binding assays as well as for immunization, were produced similarly from the appropriate genetic constructs using standard molecular biology techniques. GST-FGF2 was purified using an anti-GST column, FGF2-Fc was purified using a protein A/G column, and FGF-Flag was used in culture supernatant after determination of the FGF2-Flag concentration. In addition, purified human FGF2 (QED Bioscience Inc.) and murine FGF2 (ProSpec-Tany Technogene Ltd.) were purchased.

Preparation of FGFR-Fc Proteins. The Extracellular Domain (ECD) of Human FGFR1 alpha (IIIc) (designated as FGFR1c) and human FGFR2c alpha (IIIc) (designated as FGFR2c) were expressed as immunoadhesin molecules. DNA fragments encoding the entire ECD of FGFR1c and FGFR2c were fused to human Fc via a polypeptide linker. These FGFR-Fc molecules were expressed by transfecting human 293F cells and selecting stable 293 transfectants in the presence of G418 (1 mg/ml) in 293 expression medium (Invitrogen). The FGFR-Fc secreted from 293F transfected cells was purified using a protein A/G column. In addition, human FGFR3c-Fc and human FGFR4-Fc fusion were obtained from R & D Systems.

Synthesis of FGF2 fragments. Peptides consisting of amino acid residues 29-44 (Peptide #1), 101-118 (Peptide #3) and 137-155 (peptide #4) of FGF2 were synthesized by SynBioSci. Extra cysteine residues were added to the c-terminus of Peptide #1 and #3 and the N-terminus of peptide #4. These peptide fragments were then conjugated to keyhole limpet hemocyanin (KLH).

FGF2 binding ELISA. ELISA wells were coated with 50 µg/ml of heparin (Sigma) overnight at 4° C. and then incubated with 0.3-1 µg/ml of either human or mouse FGF2 for 1 hr at room temperature (RT) so that the heparin could capture the FGF2. After blocking with 2% BSA for 1 hr at RT, hybridoma culture supernatants or purified mAbs were added for 1 hr at RT. The bound anti-FGF2 antibodies were detected by the addition of HRP-goat anti-mouse IgG Fc for 1 hr at RT, followed by washing, addition of TMB substrate (Sigma) and reading at 450 nm.

FGFR-Fc/FGF2-Flag Binding ELISA. The blocking activity of anti-FGF2 mAbs was determined in the FGFR-Fc/FGF2-Flag binding ELISA. ELISA wells were coated with 2 µg/ml of goat antibody specific for human IgG-Fc overnight at 4 C. After blocking with 2% BSA for 1 hr at RT, the wells were incubated with 0.5 µg/ml of FGFR1c-Fc, FGFR2c-Fc, FGFR3c-Fc or FGFR4-Fc for 1 hr. After washing, wells were incubated with FGF2-Flag (0.2 µg/ml) in the presence of various concentrations of mAbs for 1 hr. The bound FGF2-Flag was detected by the addition of HRP-anti-Flag M2 antibody (Sigma).

Example 2

Generation of Monoclonal Antibodies

Balb/c mice (5-6 week old female) were immunized by injection in their rear footpads 14 times at 1 week intervals with GST-FGF2, FGF2-Fc and/or KLH conjugated FGF2 synthetic peptides, resuspended in MPL/TDM (Sigma-Aldrich), as described in the table below. Three days after the final injection, popliteal lymphoid cells were fused with P3/X63-Ag8U1 mouse myeloma cells using standard fusion methods with 35% polyethylene glycol as described (Chuntharapai et al., Methods Enzymol 288:15, 1997). Ten days after the fusion, hybridoma culture supernatants were screened for their ability to bind to FGF2 using the FGF2 binding ELISA described above. Selected mAbs were then screened for their blocking activities in the FGFR1-Fc/FGF-Flag binding ELISA. Selected hybridomas were then cloned twice using the limiting dilution technique as described (Harlow et al., 1988).

TABLE

Immunization protocol

| Injection No. | Antigens (in MPL/TDM) per footpad |
|---|---|
| 1 | GST-FGF2 10 μg |
| 2 | GST-FGF2 5 μg |
| 3 | GST-FGF2 2.5 μg |
| 4-7 | GST-FGF2 5 μg |
| 8-9 | GST-FGF2 10 μg |
| 10 | GST-FGF2 (5 μg) + FGF2-Fc (5 μg) |
| 11 | FGF2-Fc (2 μg) + Peptide #1 & # 3 (2 μg) |
| 12 | FGF2-Fc (2 μg) + Peptide #1, #3 & #4 (3 μg) |
| 13 | FGF2-Fc (2 μg) + Peptide #1, #3 & #4 (3 μg) |
| 14 | FGF2-Fc 2 μg |

Figure 2:
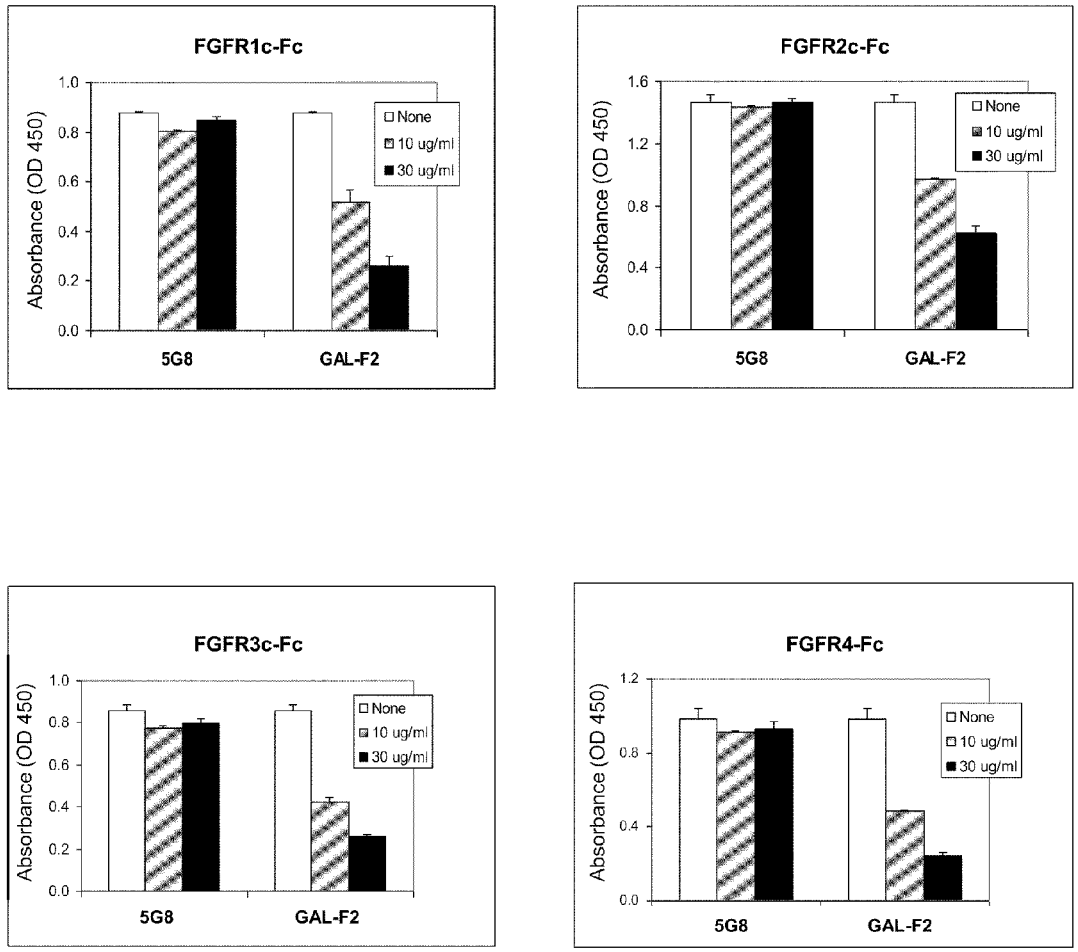
FIG. 2. FGFR-Fc/FGF2-Flag Binding ELISA showing inhibition by GAL-F2 but not control mouse mAb 5G8 for each of the four FGF receptors FGFR1-4.

FIG. 1 shows that the mAb GAL-F2 generated in this way binds to both human and mouse FGF2, approximately equally well, whereas a negative control mouse IgG mAb does not bind to FGF2. FIG. 2 shows that GAL-F2 but not the control mAb 5G8 is able to inhibit binding of human FGF2 to each of the four FGF receptors FGFR1-4. In another experiment using the FGFR-Fc/FGF2-Flag Binding ELISA described above, GAL-F2 (at a concentration of 10 μg/ml) completely inhibited the binding of FGF2 to each of the four FGFRs—FGFR1, FGFR2, FGFR3 and FGFR4—that is, reduced the signal to background level within experimental error, while the anti-FGF2 mAbs bFM-1 and 3H3 reduced binding substantially but not completely.

Example 3

Epitope of GAL-F2

Figure 3:
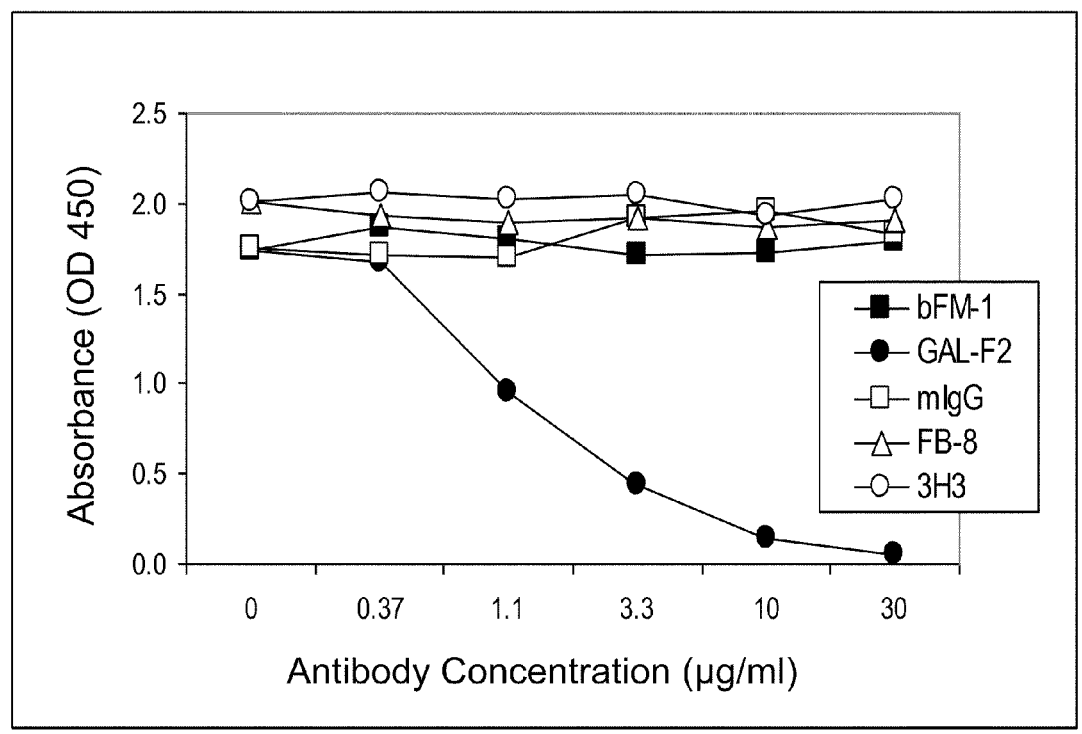
FIG. 3. Competitive binding assay of biotinylated GAL F2 to human FGF2 with various anti-FGF2 mAbs.

Several commercially available anti-FGF2 mAbs that have been reported to have certain neutralizing activities—3H3 (Calbiochem), mAb bFM-1 (Millipore) and mAb FB-8 (Abcam)—were purchased. A competitive binding ELISA was performed to determine if GAL-F2 has the same epitope as any of these mAbs. ELISA plates were coated with 50 μl/well of heparin (50 μg/ml) overnight, decanted and incubated with 50 μl/well of FGF2 for 1 hr. After blocking with 2% BSA, wells were incubated with 0.5 μg/ml of biotinylated GAL-F2 mAb in the presence of various concentrations of each anti-FGF2 mAb to be tested. The level of biotinylated GAL-F2 binding to the FGF2 in each well was detected by the addition of HRP-streptavidin followed by TMB substrate. FIG. 3 shows that none of the mAbs 3H3, bFM-1 and FB-8 nor a negative control mouse mAb (mIgG) competed for binding to FGF2 with GAL-F2, while of course GAL F2 competed with itself. Hence no previous anti-FGF2 mAb tested has the same or overlapping epitope on FGF2 as GAL-F2.

Example 4

Inhibition of FGF2-induced Proliferation by GAL-F2

BaF3 cells (DSMZ, Germany) are maintained in RPMI 1640 medium (GIBCO) supplemented with 10% FCS, 10% WEHI-3 conditioned medium and antibiotics. Stable FGFR1c or FGFR2c expressing Ba/F3 cells were generated by electroporation of linearized FGFR1c and FGFR2c expression vector DNAs as described (Ornitz et al., 1996). Stable transfected cells are selected using G418 (600 μg/ml) for 10 days. The stable Ba/F3 transfectants expressing FGFR1c or FGFR2c were shown to proliferate in response to FGF2 in the absence of WEHI-3 medium. To determine the blocking (neutralizing) activity of GAL-F2 mAb, the FGFR1c- or FGFR2c-expressing BaF3 cells (10,000 cells/well) were washed and resuspended in RPMI with 10% FCS plus 2 μg/ml of heparin and 20 ng/ml of FGF-2 in the presence of various concentrations of GAL-F2. After incubation for 36-48 hrs at 37° C., 5% $CO_2$, the level of proliferation was determined by the addition of WST-1 (Roche Applied Science) for 2 hrs. FIG. 4 shows that GAL F2 inhibited FGF2-induced proliferation, almost completely at 10 μg/ml mAb.

Figure 5:
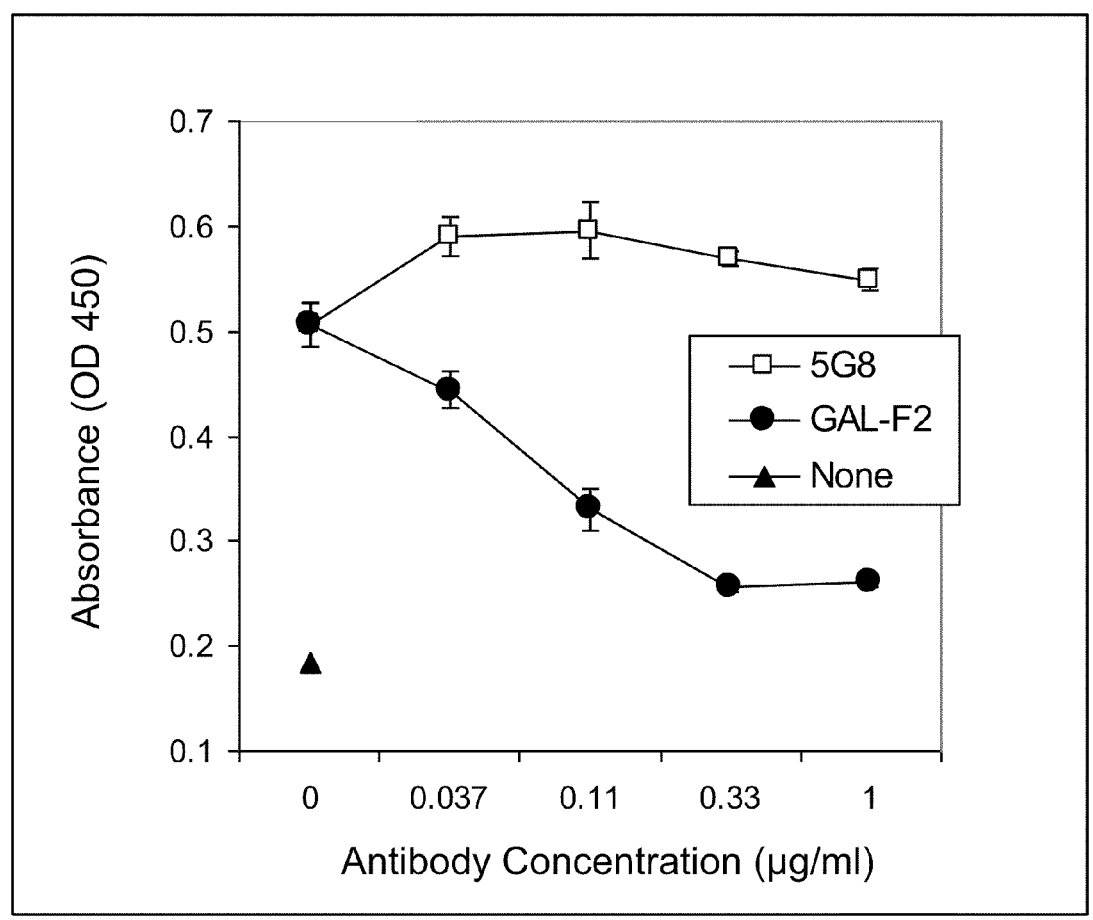
FIG. 5. Inhibition of FGF2-induced proliferation of Mv 1 Lu mink lung epithelial cells by GAL-F2 or control mAb 5G8. None means that no FGF2 (or mAb) was applied to the cells.

The blocking activities GAL-F2 on normal epithelial cells were determined using Mv 1 Lu mink lung epithelial cells (CCL-64 from ATCC). Mv 1 Lu cells (2×103 cells/100 μl/well) grown in DMEM containing 10% FCS were resuspended in serum-free DMEM and stimulated with 1-2 ng/ml of FGF2, plus 1 ng/ml of TGF-β to inhibit background proliferation, in the presence of various concentrations of mAb for 24 hrs. The level of cell proliferation was determined by the addition of WST-1 (Roche Applied Science) for 24-48 hr. FIG. 5 shows that GAL-F2 inhibited FGF2-induced proliferation of the Mv 1 Lu cells, almost completely at 1 μg/ml mAb. In a similar experiment, GAL-F2 inhibited proliferation of HUVEC induced by 10 ng/ml FGF2, by about 75% at a concentration of 0.1 μg/ml (i.e., at an approximately equimolar ratio to FGF2) and completely at a concentration of 1.0 μg/ml. This was somewhat better than the extent of inhibition by the bFM-1 anti-FGF2 mAb and substantially better than by the 3H3 anti-FGF2 mAb, and suggests that GAL-F2 inhibits angiogenesis, since proliferation of endothelial cells is an essential step in angiogenesis.

Example 5

Clonogenic Assay

The anti-tumor activity of GAL-F2 was investigated in vitro by its effect on the colony formation of human tumor cells in soft agar. The assay was performed as follows: 6-well plates was coated with 1.5 ml/well of 0.6% agar in DMEM containing 10% FCS and then layered with 1.5 ml of 0.3% agar in DMEM with 10% FCS. The top agar layer was mixed with 2×$10^4$ SMMC-7721 human hepatoma tumor cells plus 10 μg/ml of mAb. Plates were incubated at 37° C. in a humidified incubator for 10 to 14 days and then stained with 0.005% crystal violet for 1 hr and examined by photomicroscopy. FIG. 6 shows that compared to cells in the presence of irrelevant control mouse IgG mAb, cells in the presence of GAL-F2 formed many fewer colonies, while the bFM-1 anti-FGF2 mAb did not reduce the number of colonies. Hence, GAL-F2 inhibited colony formation in soft agar of human tumor cells.

Example 6

Angiogenesis Assay

The anti-angiogenic activity of GAL-F2 was determined in BALB/c mice injected in the back with 0.4 ml of matrigel (BD Biosciences) with or without 30 ng of FGF2 and/or 3 µg GAL-F2. Matrigel plugs were harvested for photography on day 6. FGF2 stimulated the formation of blood vessels in this assay, while GAL-F2 at least partially inhibited this stimulation.

Example 7

Xenograft Models

Xenograft experiments are carried out as described previously (Kim et al., Nature 362:841, 1993). Human tumor cells typically grown in complete DMEM medium are harvested in HBSS. Female athymic nude mice or NIH-III Xid/Beige/nude mice (4-6 wks old) are injected subcutaneously with 2-10×10$^6$ cells in 0.1 ml of HBSS in the dorsal areas. When the tumor size reaches 50-100 mm$^3$, the mice are grouped randomly and 5 mg/kg (100 µg total) of mAbs are administered i.p. twice per week in a volume of 0.1 ml. Tumor sizes are determined twice a week by measuring in two dimensions [length (a) and width (b)]. Tumor volume is calculated according to V=ab2/2 and expressed as mean tumor volume±SEM. The number of mice in each treatment group is typically 5-7 mice. Statistical analysis can be performed, e.g., using Student's t test.

Figure 7:
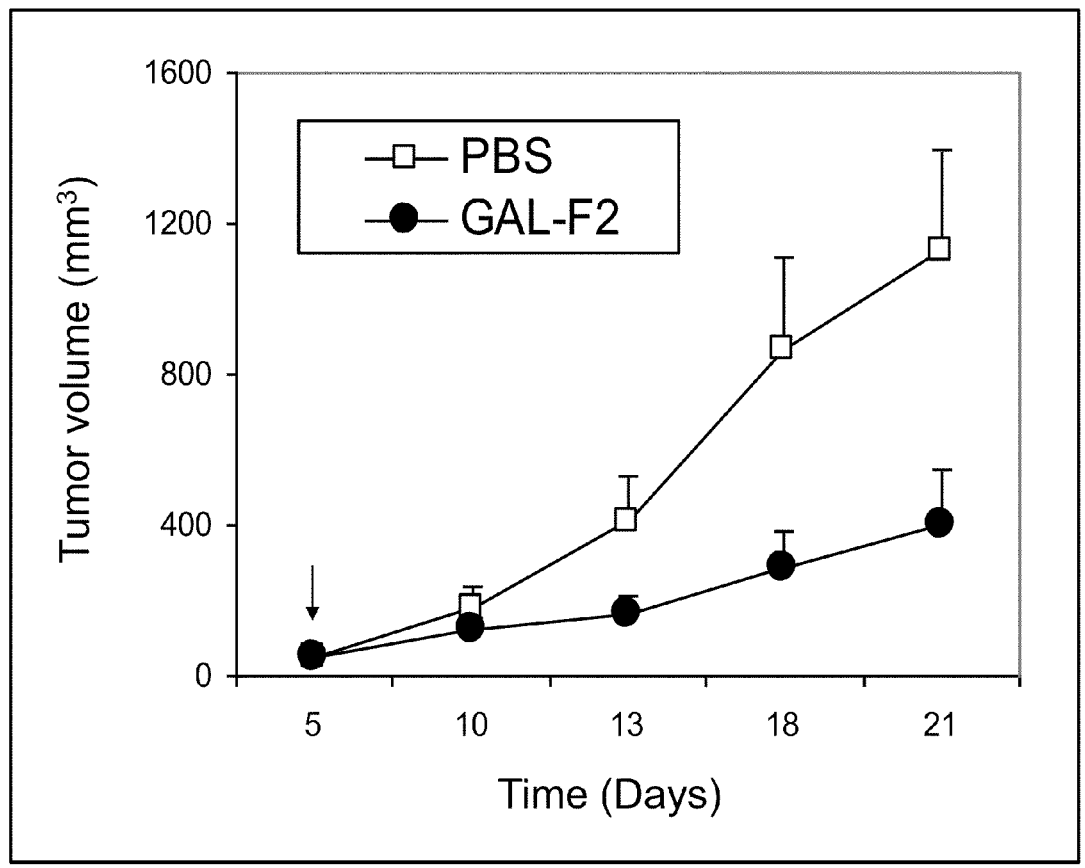
FIG. 7. Growth of RPMI 4788 human colon tumor xenografts in mice treated with GAL-F2 (100 µg twice per week) or PBS alone starting from 5 days after tumor inoculation.
Figure 8:
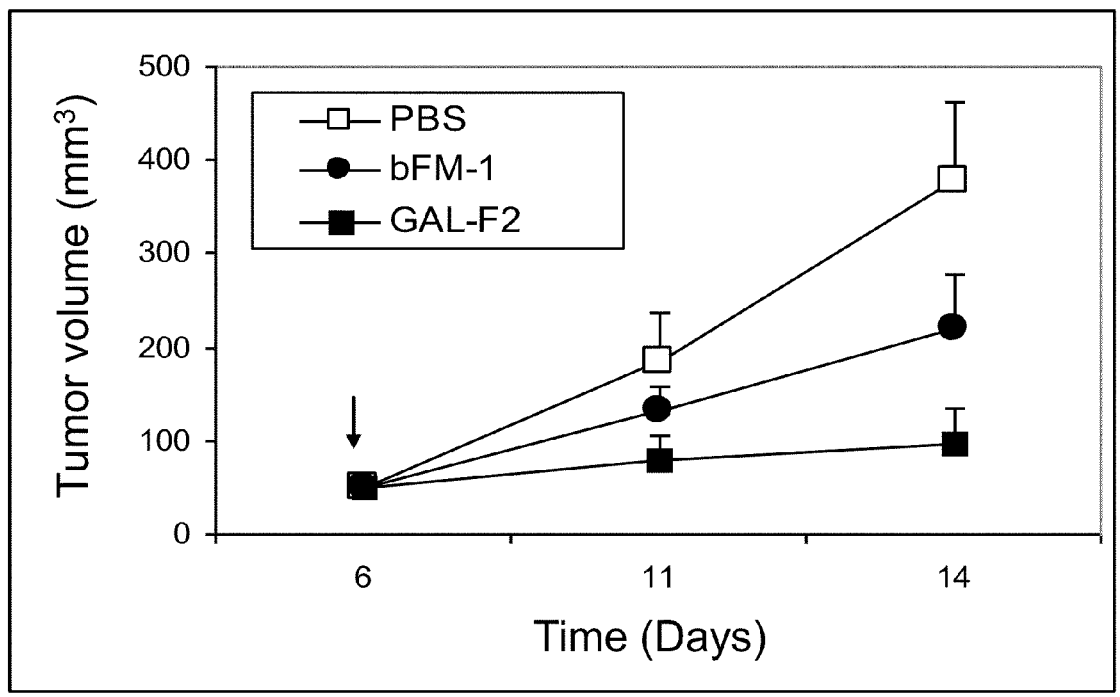
FIG. 8. Growth of RPMI 4788 human colon tumor xenografts in mice treated with GAL-F2 or bFM-1 anti-FGF2 mAb (100 µg twice per week) or PBS alone, starting from 6 days after tumor inoculation.
Figure 9:
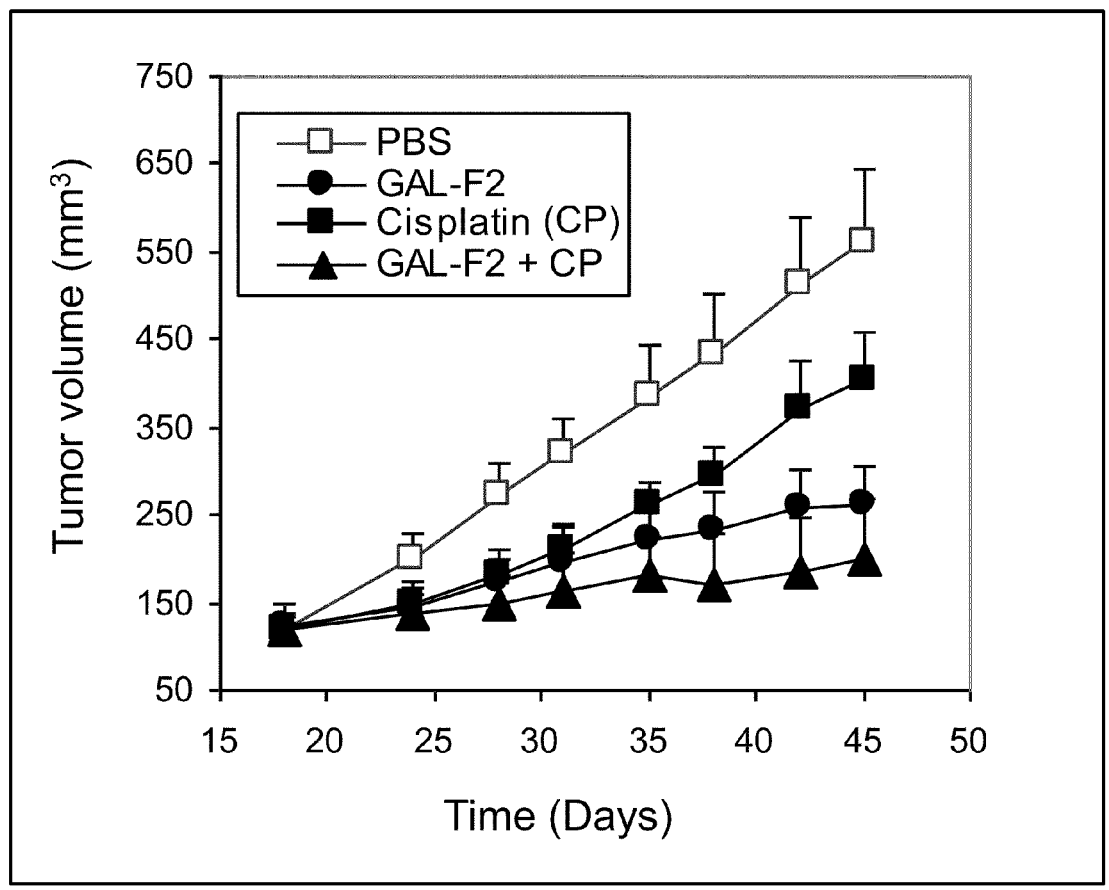
FIG. 9. Growth of SMMC-7721 human hepatoma tumor xenografts in mice treated with PBS alone, GAL-F2 (100 µg twice per week), cisplatin (100 µg once per week), or both GAL-F2 and cisplatin. 5 mice per group.
Figure 10:
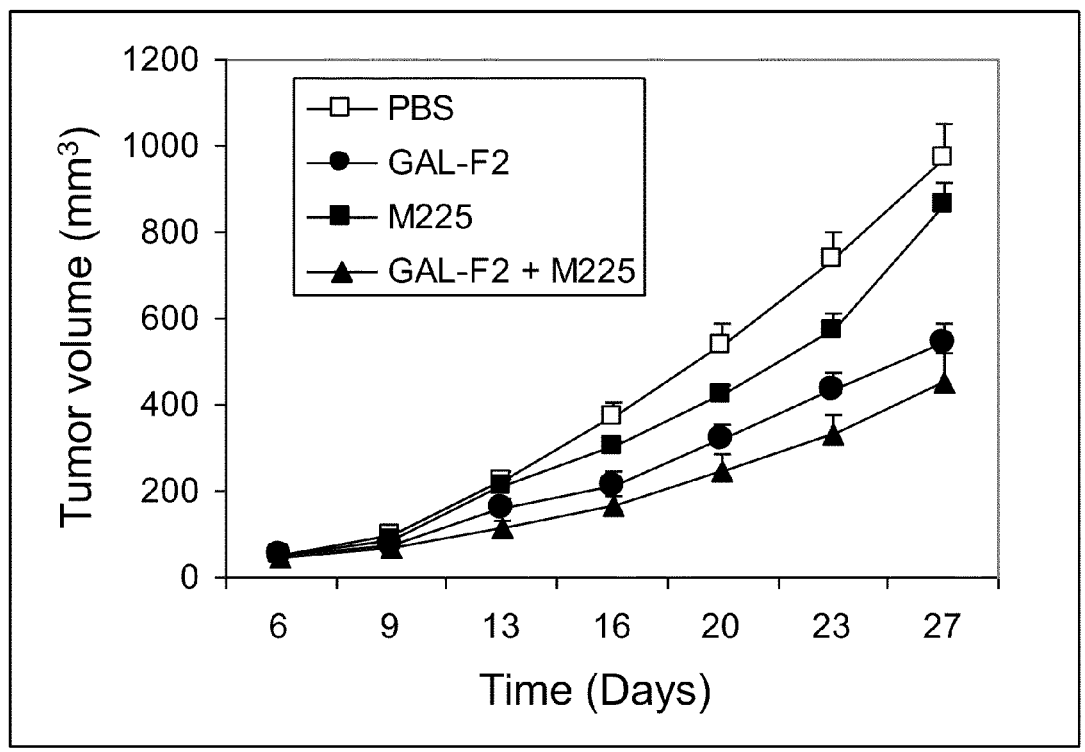
FIG. 10. Growth of HepG2 human hepatoma tumor xenografts in mice treated with PBS alone, GAL-F2 or M225 anti-EGFR mAb (100 µg twice per week), or both GAL-F2 and M225, starting from 6 days after inoculation. 6 mice per group.

FIG. 7 shows that GAL-F2 strongly inhibited the growth of RPMI 4788 colon tumor xenografts, and FIG. 8 shows that the bFM-1 anti-FGF2 mAb inhibited xenograft growth to a lesser extent than GAL-F2. FIG. 9 shows that GAL-F2 inhibited SMMC-7721 hepatoma tumor xenografts in Xid/Beige/nude mice, while the chemotherapeutic drug cisplatin at 5 mg/kg once per week inhibited xenograft growth to a lesser extent. The combination of GAL-F2 and cisplatin inhibited more strongly than either agent alone, showing an additive or synergistic effect of these agents. FIG. 10 shows that GAL-F2 inhibited HepG2 hepatoma tumor xenografts in nude mice more strongly than the anti-EGF receptor mAb M225 from which Erbitux® was derived, but the combination of GAL-F2 and M225 inhibited somewhat more strongly than either agent, again showing an additive or synergistic effect of these agents. However, GAL F2 was not able to inhibit the growth of all xenografts tested, possibly because they are not dependent on FGF2 for their growth.

Example 8

Humanization of GAL-F2

Cloning of the light and heavy chain variable regions of the GAL-F2 mAb, construction and expression of a chimeric mAb, and design, construction, expression and purification of a humanized GAL-F2 mAb were all performed using standard methods of molecular biology, e.g. as described in U.S. patent application Ser. No. 11/731,774 for the L2G7 mAb, which is herein incorporated by reference for all purposes. The amino acid sequences of the (mature) light and heavy chain variable (V) regions of GAL-F2 are shown respectively in FIGS. 11A and 11B, top lines labeled GAL-F2. More specifically, to design a humanized GAL-F2 mAb, the methods of Queen et al., U.S. Pat. Nos. 5,530,101 and 5,585,089 were generally followed. The human Vκ sequence ABA70776 and VH sequence AAL04519, as shown respectively in FIGS. 11A and 11B, bottom lines, were respectively chosen to serve as acceptor sequences for the GAL-F2 VL and VH sequences because they have particularly high framework homology (i.e., sequence identity) to them. A computer-generated molecular model of the GAL-F2 variable domain was used to locate the amino acids in the GAL-F2 framework that are close enough to the CDRs to potentially interact with them. To design the humanized GAL-F2 light and heavy chain variable regions, the CDRs from the mouse GAL-F2 mAb were first conceptually grafted into the acceptor framework regions. At framework positions where the computer model suggested significant contact with the CDRs, which may be needed to maintain the CDR conformation, the amino acids from the mouse antibody were substituted for the human framework amino acids. For the humanized GAL-F2 mAb designated HuGAL-F2, this was done at residues 1, 27 and 30 (residues 27 and 30 being within Chothia hypervariable loop H1), 48, 67, 71 and 94 of the heavy chain and at no residues in the light chain, using Kabat numbering. The light and heavy chain V region sequences of HuGAL-F2 are shown in FIGS. 11A and 11B respectively, middle lines labeled HuGAL-F2, where they are aligned against the respective GAL-F2 donor and human acceptor V regions—the CDRs (as defined by Kabat) are underlined and the substituted amino acids listed above are double-underlined.

The invention provides not only a humanized GAL-F2 mAb HuGAL-F2 including the light and heavy chain V regions shown in FIG. 11, but also variant humanized GAL-F2 mAbs whose light and heavy chain variable regions differ from the sequences of HuGAL-F2 by a small number (e.g., typically no more than 1, 2, 3, 5 or 10) of replacements, deletions or insertions, usually in the framework but possibly in the CDRs. In particular, only a subset of the substitutions described above can be made in the acceptor frameworks, or additional substitution(s) can be made, e.g., the mouse GAL-F2 VH amino acid 69L may replace the acceptor amino acid 69I, or the mouse amino acids may replace the respective amino acids in the humanized light chain at any or all of the positions 1, 3, 60 and/or 67 by Kabat numbering. On the other hand, the VH amino acid 1E (Glu) may instead be Q (Gln). Indeed, many of the framework residues not in contact with the CDRs in HuGAL-F2 can accommodate substitutions of amino acids from the corresponding positions of GAL-F2 or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Most often the replacements made in the variant humanized GAL-F2 sequences are conservative with respect to the replaced HuGAL-F2 amino acids. Amino acids can be grouped as follows for determining conservative substitutions, i.e., substitutions within a group: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg;

Group V (residues influencing chain orientation): gly, pro; and Group VI (aromatic side chains): trp, tyr, phe.

Preferably, replacements in HuGAL-F2 (whether or not conservative) have no substantial effect on the binding affinity or potency of the humanized mAb, that is, its ability to neutralize the biological activities of FGF2 (e.g., the potency in some or all of the assays described herein of the variant humanized GAL-F2 mAb is essentially the same, i.e., within experimental error, as that of HuGAL-F2). Preferably the mature variant light and heavy chain V region sequences are at least 90%, more preferably at least 95%, and most preferably at least 98% identical to the respective HuGAL-F2 mature light and heavy chain V regions. Alternatively, other human antibody variable regions with high sequence identity to those of GAL-F2 are also suitable to provide the humanized antibody framework, especially kappa V regions from human subgroup I and heavy chain V regions from human subgroup I, or consensus sequences of these subgroups.

In other humanized antibodies, at least 1, 2, 3, 4, 5, 6 or all seven of the positions of acceptor to donor substitutions mentioned in connection with the exemplified antibody (i.e., H1, H27, H30, H48, H67, H71 and 94) are preferably occupied by the residue occupying the corresponding position of the mouse donor antibody heavy chain. If the heavy chain acceptor sequence is other than AAL04519 an acceptor to donor substitution may or may not be required for the specified occupancy of a particular variable framework region position depending whether the residue occupying the specified position is already the same between the acceptor and donor.

Figure 13:
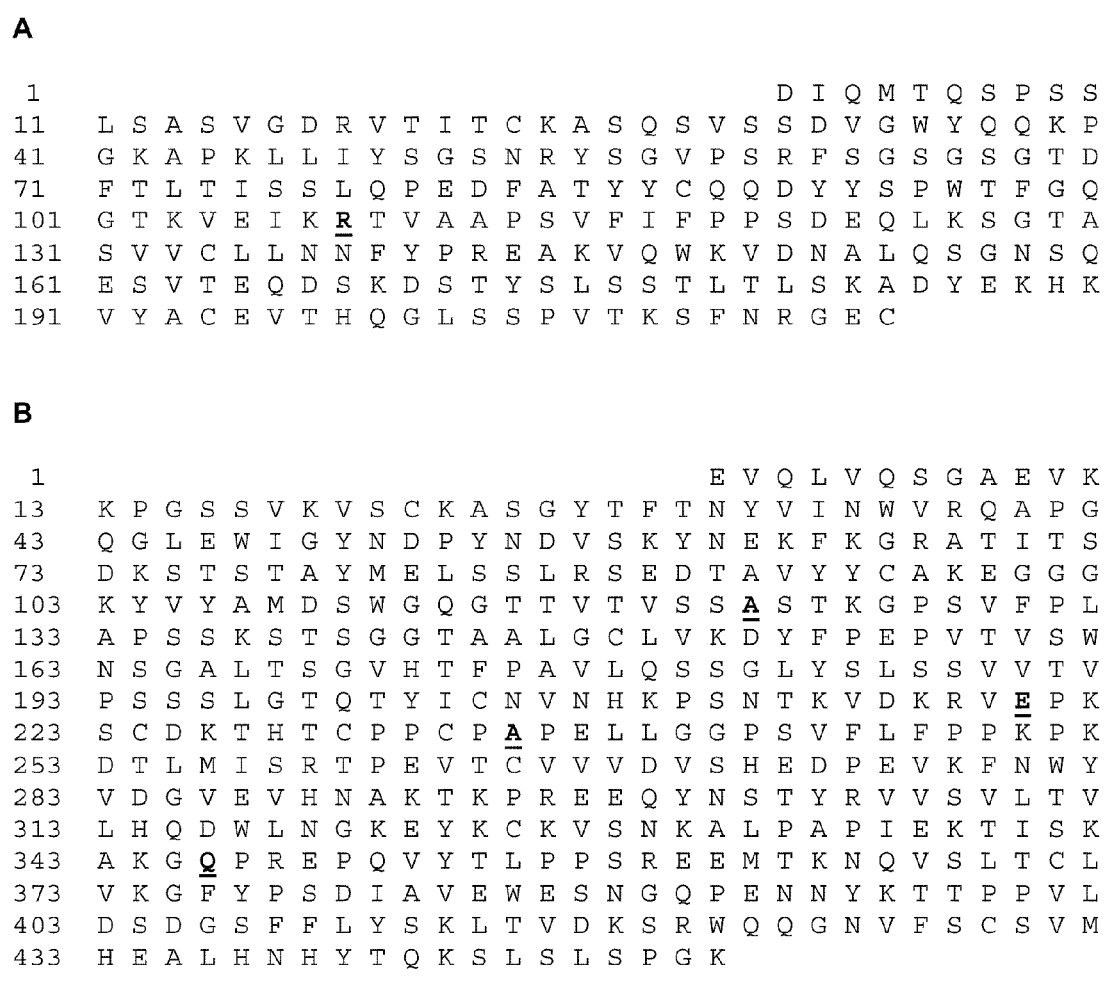

The exemplary mAb HuGAL-F2 discussed here has human κ and γ1 constant regions, e.g., as presented in U.S. patent application Ser. No. 11/731,774, and is therefore an IgG1. The complete sequences of the (mature) light and heavy chains of HuGAL-F2 are shown in FIG. 13. Thus, an exemplary humanized antibody comprises a light chain of SEQ ID NO:7 and a heavy chain of SEQ ID NO:8. While these sequences are respectively of the Km(3) and G1m(3) allotypes, it is understood that IgG1 mAbs of any (IgG1, κ) allotype are encompassed by the designation HuGAL-F2. It will also be understood that when HuGAL-F2 is manufactured by conventional procedures, one to several amino acids at the amino or carboxy terminus of the light and/or heavy chain, such as the C-terminal lysine of the heavy chain, may be missing or derivatized in a proportion or all of the molecules, and such a composition will still be encompassed by the designation HuGAL-F2 and considered a humanized GAL-F2 mAb. Humanized mAbs of other isotypes (e.g., IgG2, IgG3 and IgG4) can be made by combining the HuGAL-F2 variable regions with the appropriate human constant regions. Replacements can be made in the HuGAL-F2 constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103: 4005, 2006), or to prolong half-life in humans (see, e.g., Hinton et al., J. Biol. Chem. 279:6213, 2004). Specifically but without limitation, HuGAL-F2 having mutations in the IgG constant region to a Gln at position 250 and/or a Leu at position 428 are embodiments of the present invention.

Figure 12:
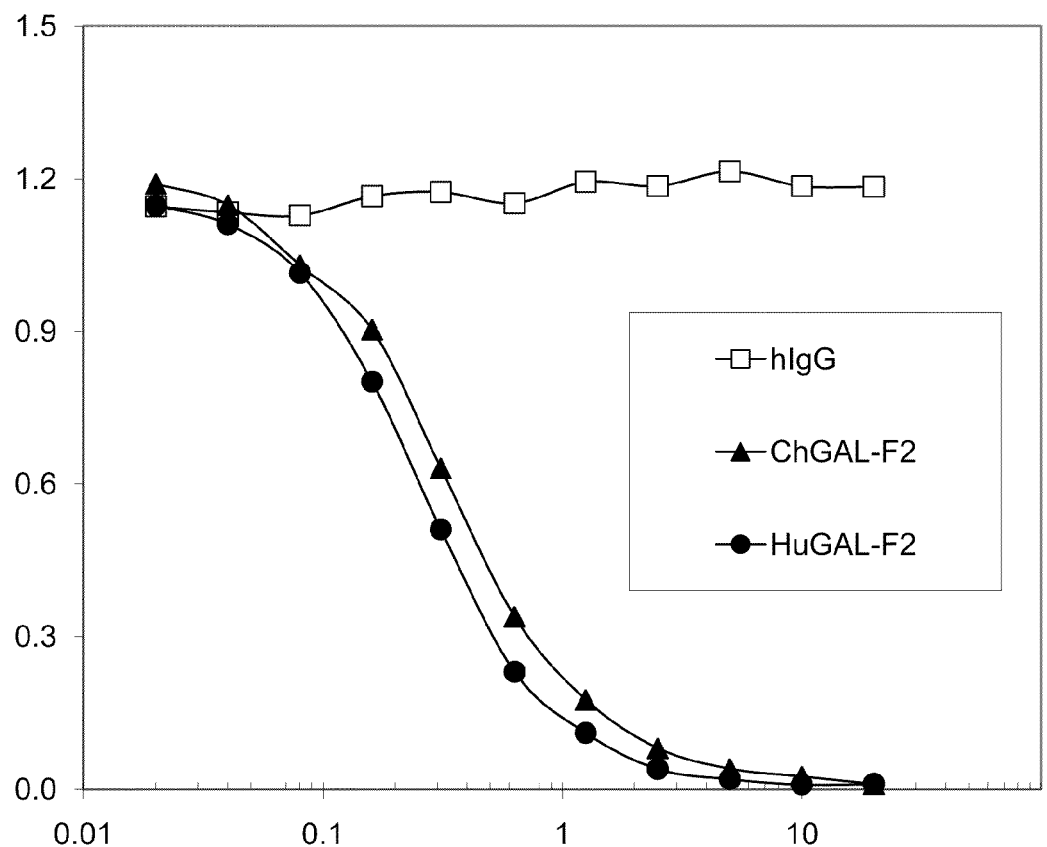
FIG. 12. Competitive binding of humanized (HuGAL-F2) and chimeric (ChGAL-F2) mAbs and control human antibody hIgG, conducted as described in the specification.

To compare the binding affinity of HuGAL-F2 with that of the mouse-human chimeric mAb ChGAL-F2, a competitive binding experiment was performed using standard ELISA technology. Specifically, human FGF2 was immobilized on a heparin-coated ELISA plate. The wells were incubated with biotinylated GAL-F2 mAb (0.5 µg/ml) in the presence of increasing concentrations of unlabeled ChGAL-F2, HuGAL-F2 or control human antibody hIgG. The level of biotinylated GAL-F2 bound was determined by the addition of HRP-streptavidin and substrate. As shown in FIG. 12, HuGAL-F2 and ChGAL-F2 competed approximately equally well, with HuGAL-F2 possibly slightly better, indicating that the binding affinity for FGF2 of HuGAL-F2 is at least as high as ChGAL-F2 and therefore as the original mouse GAL-F2 mAb. From the concentration of HuGAL-F2 required to inhibit binding of the labeled mAb by 50%, one may estimate that the binding affinity Ka of HuGAL-F2 for FGF2 is at least approximately $10^9$ $M^{-1}$. HuGAL-F2 may also be tested in any of the biological assays for FGF2 activity described herein, and will inhibit FGF2 activity comparably to the GAL-F2 mAb.

Although the invention has been described with reference to the presently preferred embodiments, it should be understood that various modifications can be made without departing from the invention. Unless otherwise apparent from the context any step, element, embodiment, feature or aspect of the invention can be used with any other. All publications, patents and patent applications including accession numbers and the like cited are herein incorporated by reference in their entirety for all purposes to the same extent as if each individual publication, patent and patent application was specifically and individually indicated to be incorporated by reference in its entirety for all purposes. If more than one sequence is associated with an accession number at different times, the sequence associated with the accession number as of May 29, 2008 is intended. In the event of any discrepancy between corresponding sequences in the figures and sequences listing, the figures control.

The hybridoma producing the monoclonal antibody GAL-F2, ATCC Number PTA-8864, has been deposited at the American Type Culture Collection, P.O. Box 1549 Manassas, Va. 20108, on Jan. 8, 2008 under the Budapest Treaty. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

What is claimed is:

1. A mouse, chimeric or humanized form of a mAb produced by the PTA-8864 hybridoma.

2. A humanized antibody comprising a humanized light chain comprising the three light chain CDRs from the sequence in FIG. 11A (GAL-F2) (SEQ ID NO:1) and a humanized heavy chain comprising the three heavy chain CDRs from the sequence of FIG. 11B (GAL-F2) (SEQ ID NO:4).

3. The humanized antibody of claim 2, wherein residues H1, H27, H30, H48, H67, H71 and H94 by Kabat numbering are occupied by the residue occupying the corresponding position of the heavy chain shown in FIG. 11B (GAL-F2) (SEQ ID NO:4).

4. The humanized antibody of claim 2 wherein the light chain variable region has at least 95% sequence identity to the sequence shown in FIG. 11A (HuGAL-F2) (SEQ ID NO:2) and the heavy chain has at least 95% sequence identity to the sequence shown in FIG. 11B (HuGAL-F2) (SEQ ID NO:5).

5. The humanized antibody of claim 4, wherein the light chain variable region has the sequence shown in FIG. 11A (HuGAL-F2) (SEQ ID NO:2) and the heavy chain has the sequence shown in FIG. 11B (HuGAL-F2) (SEQ ID NO:5).

* * * * *

UNITED STATES PATENT AND TRADEMARK OFFICE
CERTIFICATE OF CORRECTION

| | | |
|---|---|---|
| PATENT NO. | : 8,101,725 B2 | Page 1 of 1 |
| APPLICATION NO. | : 12/474198 | |
| DATED | : January 24, 2012 | |
| INVENTOR(S) | : Kyung Jin Kim et al. | |

It is certified that error appears in the above-identified patent and that said Letters Patent is hereby corrected as shown below:

In the Specification:

Column 4, Line 50: Delete "complementarily" and insert --complementarity--

Signed and Sealed this
Twenty-seventh Day of March, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 107
<212> TYPE: PRT
<213> ORGANISM: Mus musculus
<220> FEATURE:
```

<223> OTHER INFORMATION: GAL-F2

<400> SEQUENCE: 1

Ser Ile Val Met Thr Gln Thr Pro Lys Phe Leu Leu Val Ser Ala Gly
1               5                   10                  15

Asp Arg Val Thr Met Thr Cys Lys Ala Ser Gln Ser Val Ser Ser Asp
            20                  25                  30

Val Gly Trp Tyr Gln Gln Lys Pro Gly Gln Ser Pro Lys Leu Leu Ile
        35                  40                  45

Tyr Ser Gly Ser Asn Arg Tyr Ser Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Tyr Ser Pro Trp
                85                  90                  95

Thr Phe Gly Gly Gly Thr Lys Leu Glu Ile Lys
            100                 105

<210> SEQ ID NO 2
<211> LENGTH: 107
<212> TYPE: PRT
<213> ORGANISM: Homo sapiens
<220> FEATURE:
<223> OTHER INFORMATION: HuGAL-F2

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Ser Asp
            20                  25                  30

Val Gly Trp Tyr Gln Gln Lys Pro Gly Lys Ala Pro Lys Leu Leu Ile
        35                  40                  45

Tyr Ser Gly Ser Asn Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Tyr Ser Pro Trp
                85                  90                  95

Thr Phe Gly Gln Gly Thr Lys Val Glu Ile Lys
            100                 105

<210> SEQ ID NO 3
<211> LENGTH: 107
<212> TYPE: PRT
<213> ORGANISM: Homo sapiens
<220> FEATURE:
<223> OTHER INFORMATION: immunoglobulin kappa light chain variable
      region

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Tyr Ser Thr Pro Trp
                    85                  90                  95

Thr Phe Gly Gln Gly Thr Lys Val Glu Ile Lys
                100                 105

<210> SEQ ID NO 4
<211> LENGTH: 121
<212> TYPE: PRT
<213> ORGANISM: Mus musculus
<220> FEATURE:
<223> OTHER INFORMATION: GAL-F2

<400> SEQUENCE: 4

Glu Val His Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30

Val Ile Asn Trp Val Lys Gln Lys Pro Gly Gln Gly Leu Glu Trp Ile
            35                  40                  45

Gly Tyr Asn Asp Pro Tyr Asn Asp Val Ser Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Glu Gly Gly Gly Lys Tyr Val Tyr Ala Met Asp Ser Trp Gly
                100                 105                 110

Gln Gly Thr Ser Val Thr Val Ser Ser
        115                 120

<210> SEQ ID NO 5
<211> LENGTH: 121
<212> TYPE: PRT
<213> ORGANISM: Homo sapiens
<220> FEATURE:
<223> OTHER INFORMATION: HuGAL-F2

<400> SEQUENCE: 5

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Val Ile Asn Trp Val Arg Gln Ala Pro Gly Gln Gly Leu Glu Trp Ile
            35                  40                  45

Gly Tyr Asn Asp Pro Tyr Asn Asp Val Ser Lys Tyr Asn Glu Lys Phe
        50                  55                  60

Lys Gly Arg Ala Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Gly Lys Tyr Val Tyr Ala Met Asp Ser Trp Gly
                100                 105                 110

Gln Gly Thr Thr Val Thr Val Ser Ser
        115                 120

<210> SEQ ID NO 6
<211> LENGTH: 122
<212> TYPE: PRT
```

```
<213> ORGANISM: Homo sapiens
<220> FEATURE:
<223> OTHER INFORMATION: immunoglobulin heavy chain variable region

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Gln Leu Gly Tyr Tyr Tyr Gly Met Asp Val Trp
            100                 105                 110

Gly Gln Gly Thr Thr Val Thr Val Ser Ser
            115                 120

<210> SEQ ID NO 7
<211> LENGTH: 214
<212> TYPE: PRT
<213> ORGANISM: Homo sapiens
<220> FEATURE:
<223> OTHER INFORMATION: HuGAL-F2 antibody light chain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Ser Asp
            20                  25                  30

Val Gly Trp Tyr Gln Gln Lys Pro Gly Lys Ala Pro Lys Leu Leu Ile
        35                  40                  45

Tyr Ser Gly Ser Asn Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Tyr Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

-continued

<210> SEQ ID NO 8
<211> LENGTH: 451
<212> TYPE: PRT
<213> ORGANISM: Homo sapiens
<220> FEATURE:
<223> OTHER INFORMATION: HuGAL-F2 antibody heavy chain

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Val Ile Asn Trp Val Arg Gln Ala Pro Gly Gln Gly Leu Glu Trp Ile
        35                  40                  45

Gly Tyr Asn Asp Pro Tyr Asn Asp Val Ser Lys Tyr Asn Glu Lys Phe
    50                  55                  60

Lys Gly Arg Ala Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Lys Tyr Val Tyr Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

```
Leu Thr Cys Leu Val Lys Gly Phe Tyr Pro Ser Asp Ile Ala Val Glu
        370             375             380

Trp Glu Ser Asn Gly Gln Pro Glu Asn Asn Tyr Lys Thr Thr Pro Pro
385                 390             395             400

Val Leu Asp Ser Asp Gly Ser Phe Phe Leu Tyr Ser Lys Leu Thr Val
                405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro Gly Lys
    450
```